United States Patent
Tsuji et al.

(10) Patent No.: US 12,194,218 B2
(45) Date of Patent: Jan. 14, 2025

(54) BLOOD PURIFICATION APPARATUS

(71) Applicant: Nikkiso Company Limited, Tokyo (JP)

(72) Inventors: Kazuya Tsuji, Shizuoka (JP); Satoshi Takeuchi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 602 days.

(21) Appl. No.: 17/490,102

(22) Filed: Sep. 30, 2021

(65) Prior Publication Data

US 2022/0031922 A1    Feb. 3, 2022

Related U.S. Application Data

(63) Continuation of application No. PCT/JP2020/020980, filed on May 27, 2020.

(30) Foreign Application Priority Data

May 28, 2019   (JP) ................................ 2019-099699

(51) Int. Cl.
*A61M 1/36* (2006.01)
*A61M 1/16* (2006.01)
(Continued)

(52) U.S. Cl.
CPC ........ *A61M 1/3644* (2014.02); *A61M 1/1656* (2013.01); *A61M 1/267* (2014.02); *A61M 1/3413* (2013.01)

(58) Field of Classification Search
CPC .. A61M 1/3644; A61M 1/1656; A61M 1/267; A61M 1/341; A61M 1/168
See application file for complete search history.

(56) References Cited

U.S. PATENT DOCUMENTS

2013/0213890 A1*   8/2013  Kelly ..................... A61M 1/16
                                                            210/101

FOREIGN PATENT DOCUMENTS

| JP | 2005-124775 A | 5/2005 |
| JP | 2015-156924 A | 9/2015 |
| JP | 2017-006485 A | 1/2017 |

OTHER PUBLICATIONS

International Search Report for Application No. PCT/JP2020/020980, dated Jul. 21, 2020.

* cited by examiner

*Primary Examiner* — Thuan D Dang
(74) *Attorney, Agent, or Firm* — Young Basile Hanlon & MacFarlane, P.C.

(57) ABSTRACT

A blood purification apparatus including a line section through which working dialysate to be introduced into a blood purifier or drain liquid discharged from the blood purifier is caused to flow; a delivery unit that delivers liquid in the line section; an introduction port connected to a supply route through which undiluted dialysate or the working dialysate is supplied, the introduction port allowing the undiluted dialysate or the working dialysate in the supply route to be introduced into the apparatus; an introduction route connected to the introduction port and through which the undiluted dialysate or the working dialysate introduced from the introduction port flows into the line section; a valve unit provided to the introduction route and being capable of opening or closing the introduction route by being opened or closed; and a control unit that controls an operation of opening or closing the valve unit. The control unit is capable of executing a flushing step in which when a cleaning solution or a disinfecting solution is caused to flow through the supply route, the valve unit is opened to allow the cleaning solution or the disinfecting solution flowing in the (Continued)

supply route to flow into the introduction route and through the line section to be discharged to an outside of the apparatus.

12 Claims, 11 Drawing Sheets

(51) Int. Cl.
*A61M 1/26* (2006.01)
*A61M 1/34* (2006.01)

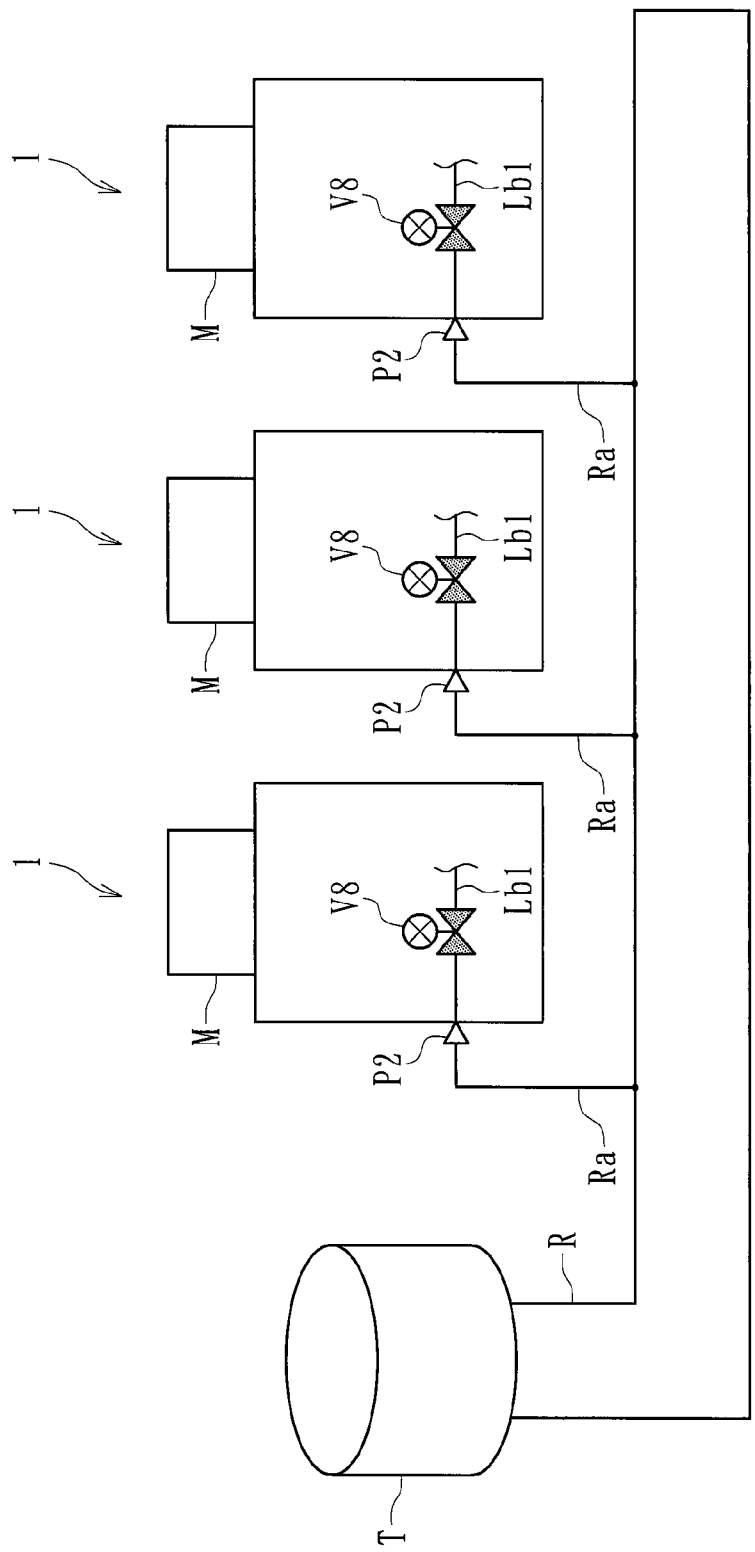
[Fig. 1]

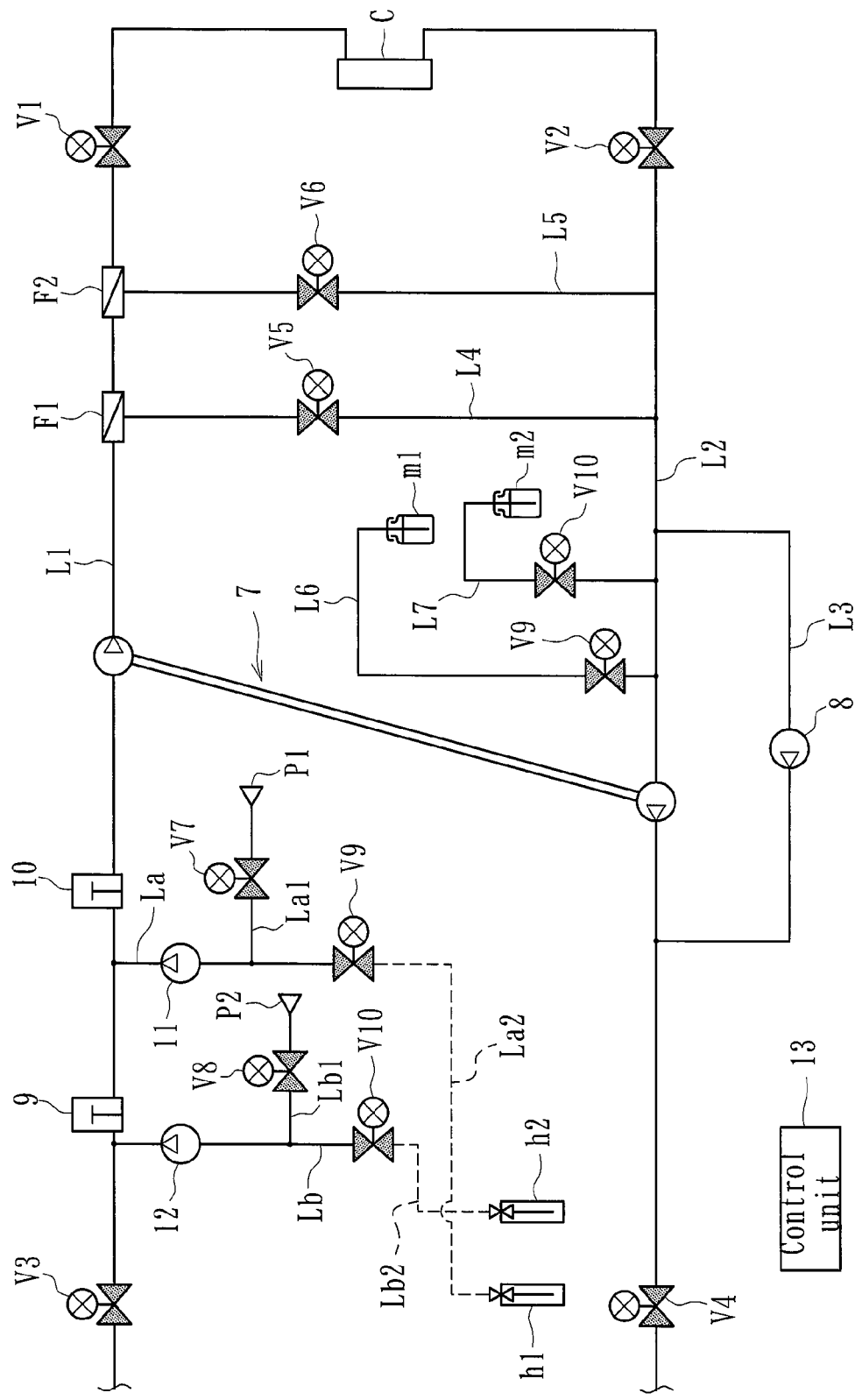
[FIG. 2]

[Fig. 3]
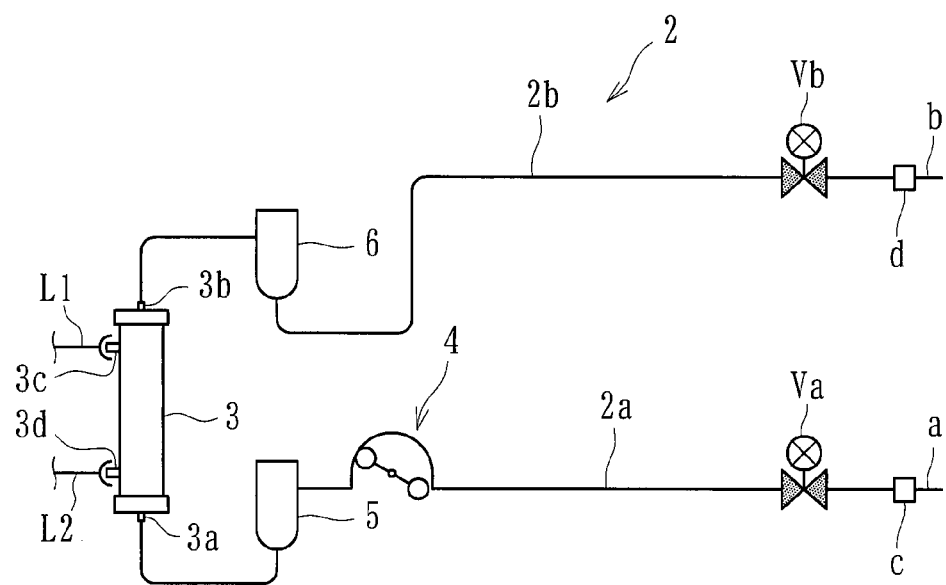
[Fig. 4]
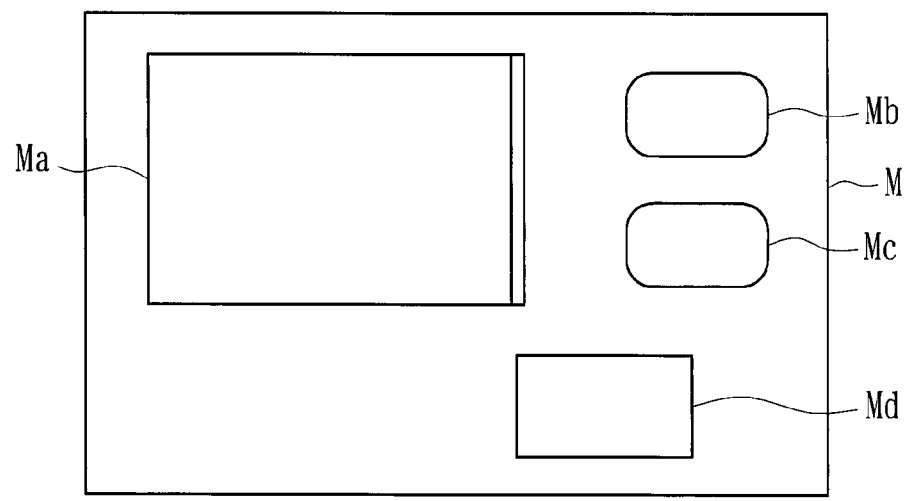

[Fig. 5]
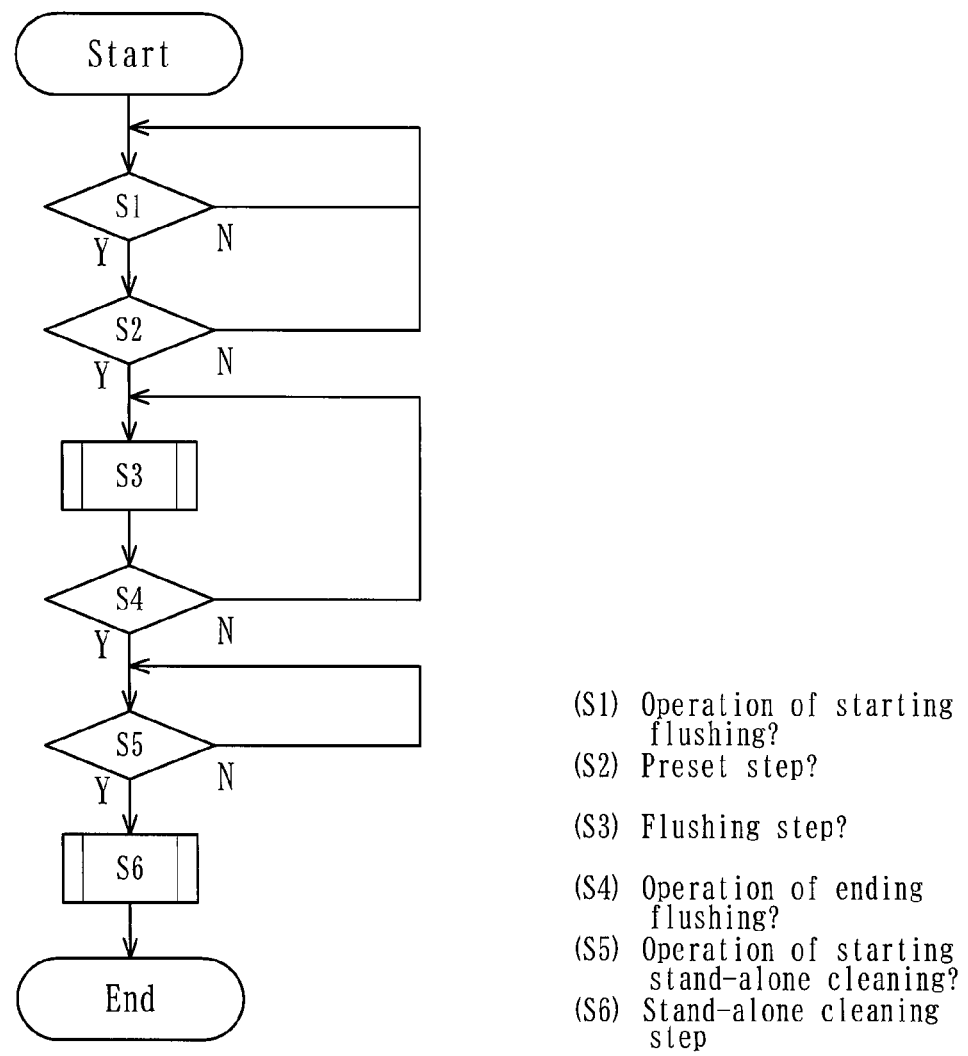
(S1) Operation of starting flushing?
(S2) Preset step?
(S3) Flushing step?
(S4) Operation of ending flushing?
(S5) Operation of starting stand-alone cleaning?
(S6) Stand-alone cleaning step

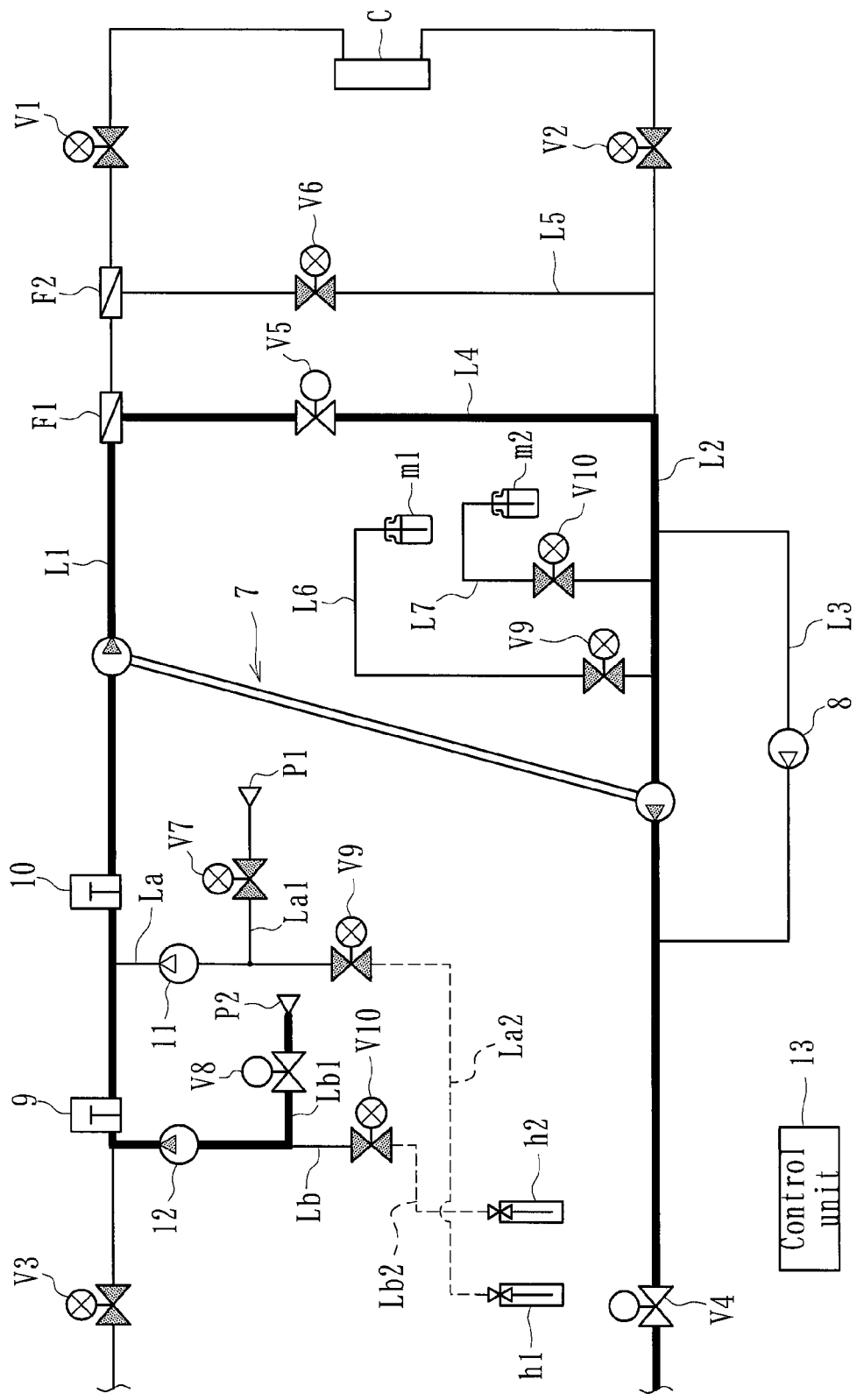
[Fig. 6]

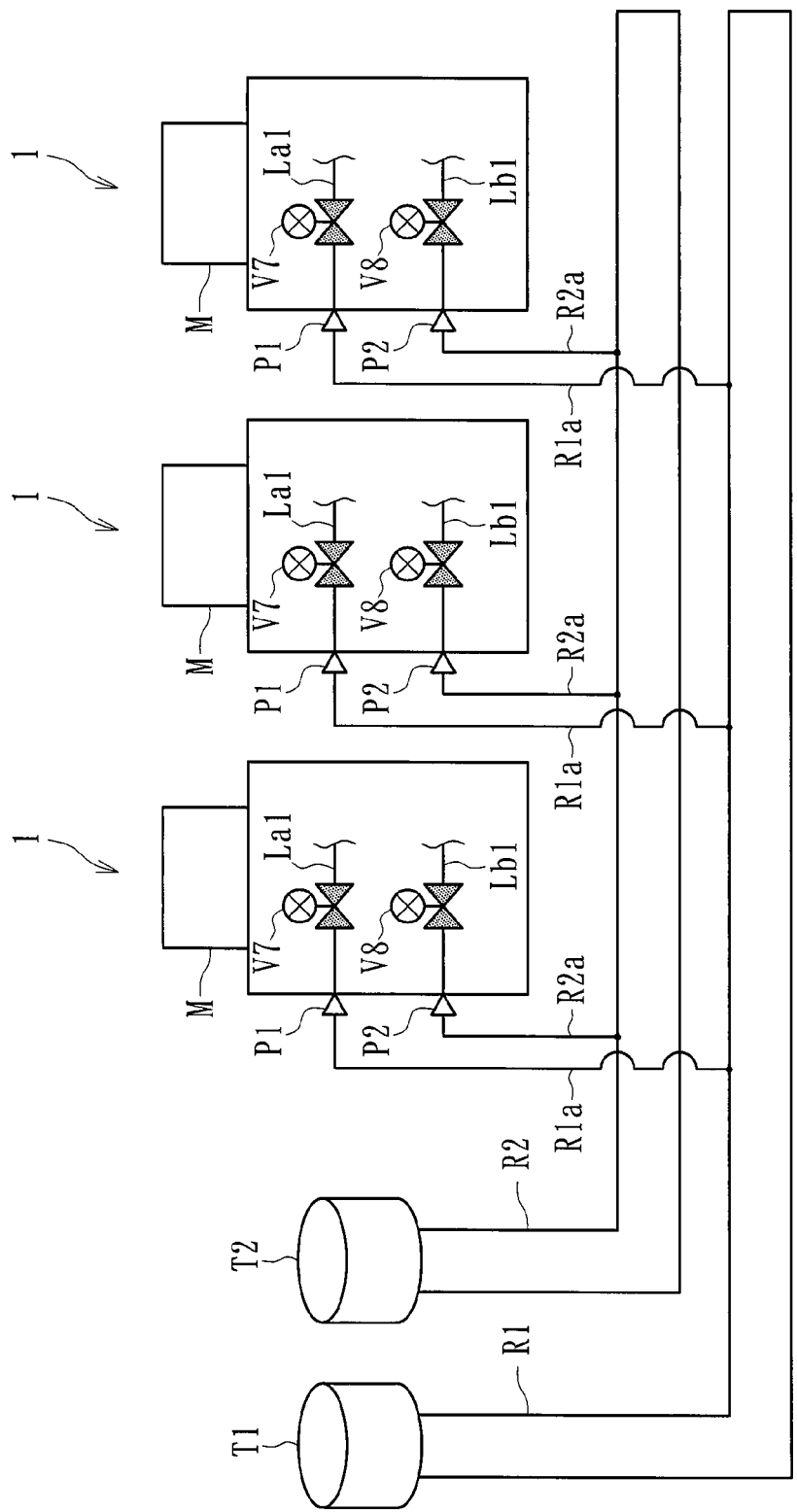
[FIG. 7]

[Fig. 8]
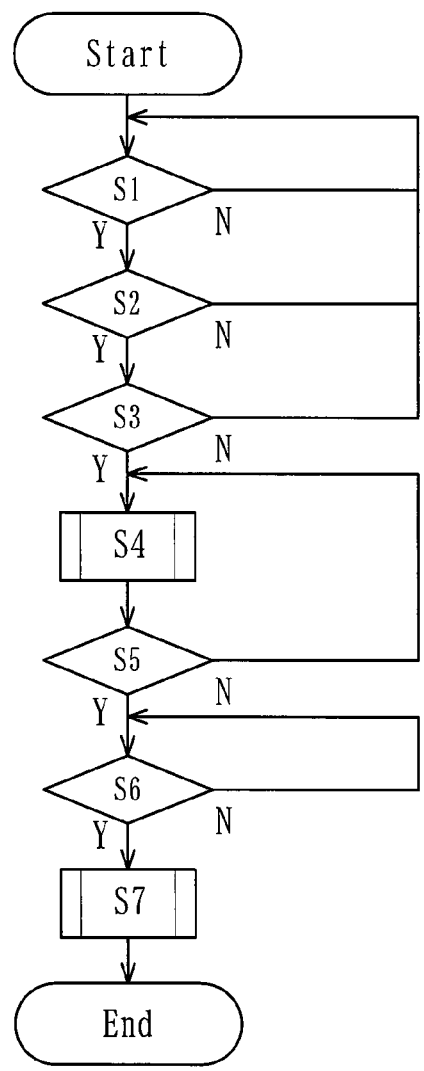
(S1) Operation of starting flushing for B-solution?
(S2) Is flushing of A-solution port stopped?
(S3) Preset step?
(S4) Flushing step?
(S5) Operation of ending flushing for B-solution?
(S6) Operation of starting stand-alone cleaning?
(S7) Stand-alone cleaning step

[Fig. 9]
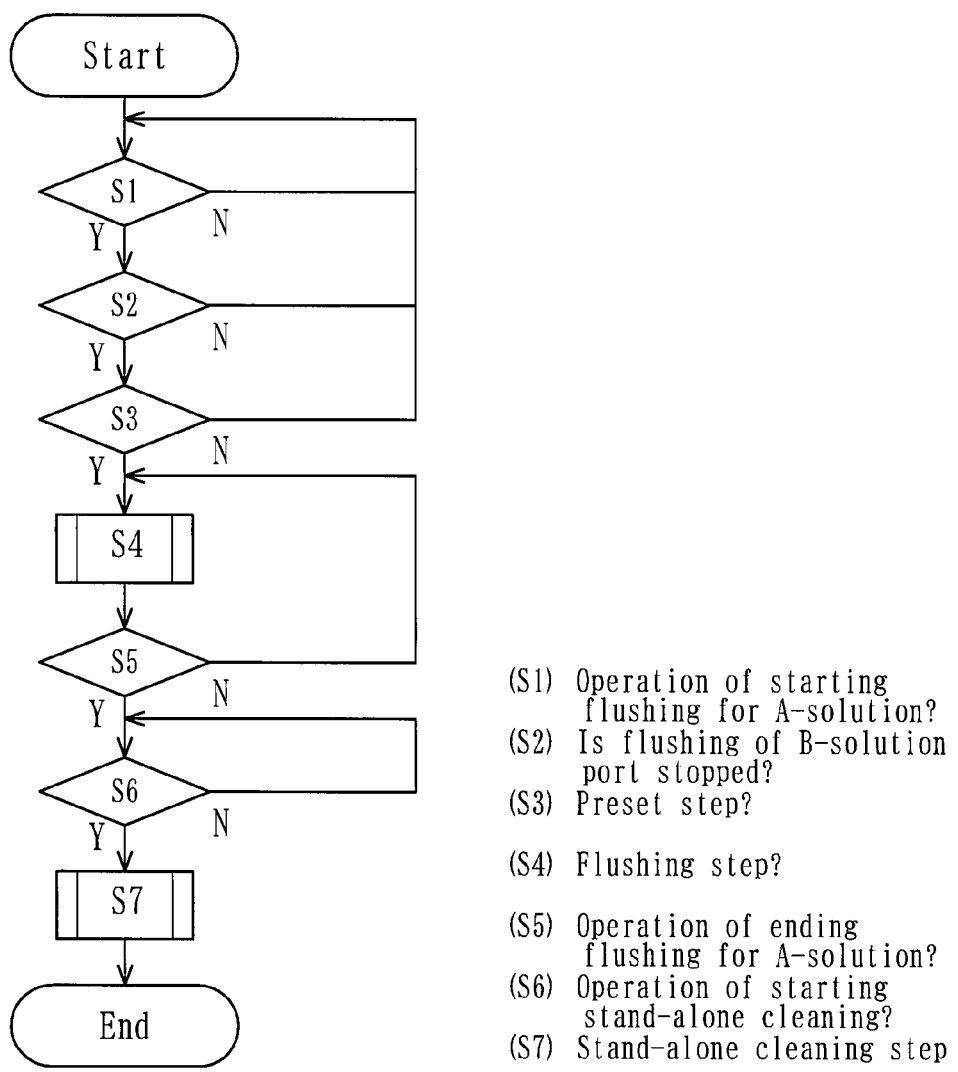
(S1) Operation of starting flushing for A-solution?
(S2) Is flushing of B-solution port stopped?
(S3) Preset step?
(S4) Flushing step?
(S5) Operation of ending flushing for A-solution?
(S6) Operation of starting stand-alone cleaning?
(S7) Stand-alone cleaning step

[Fig. 10]
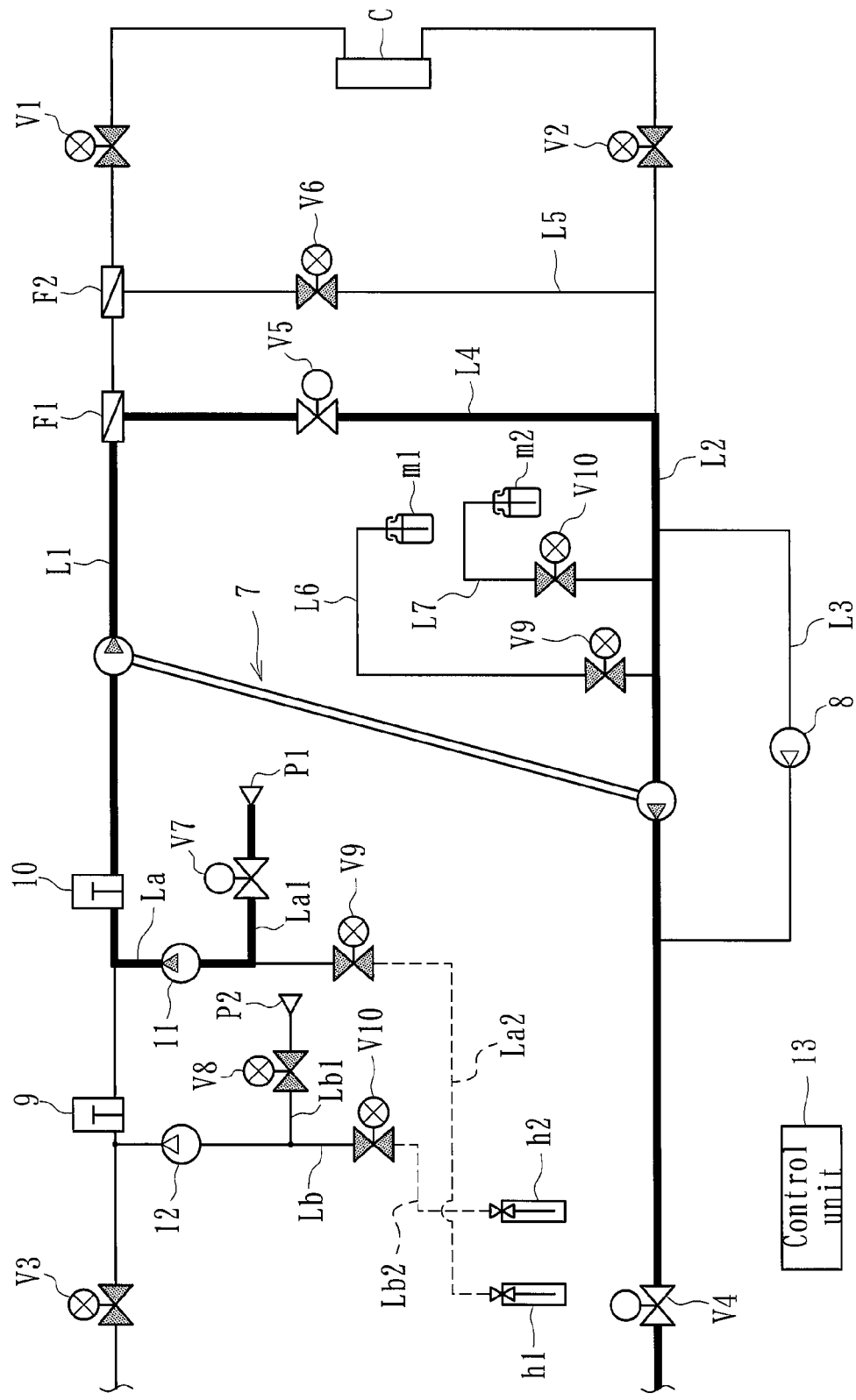

[ Fig. 11 ]
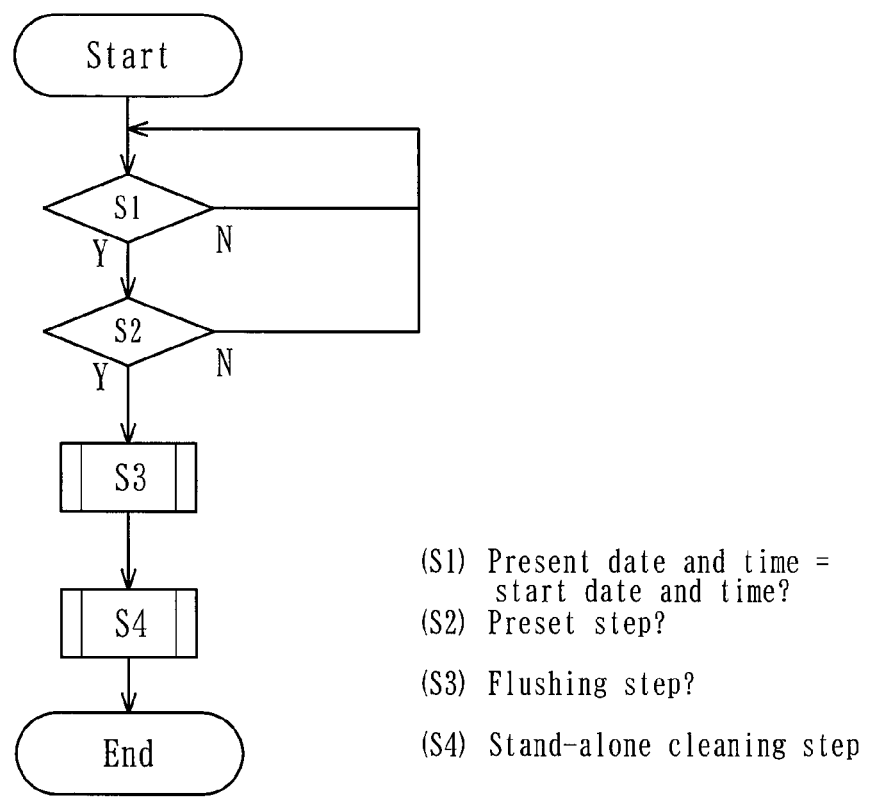

[Fig. 12]

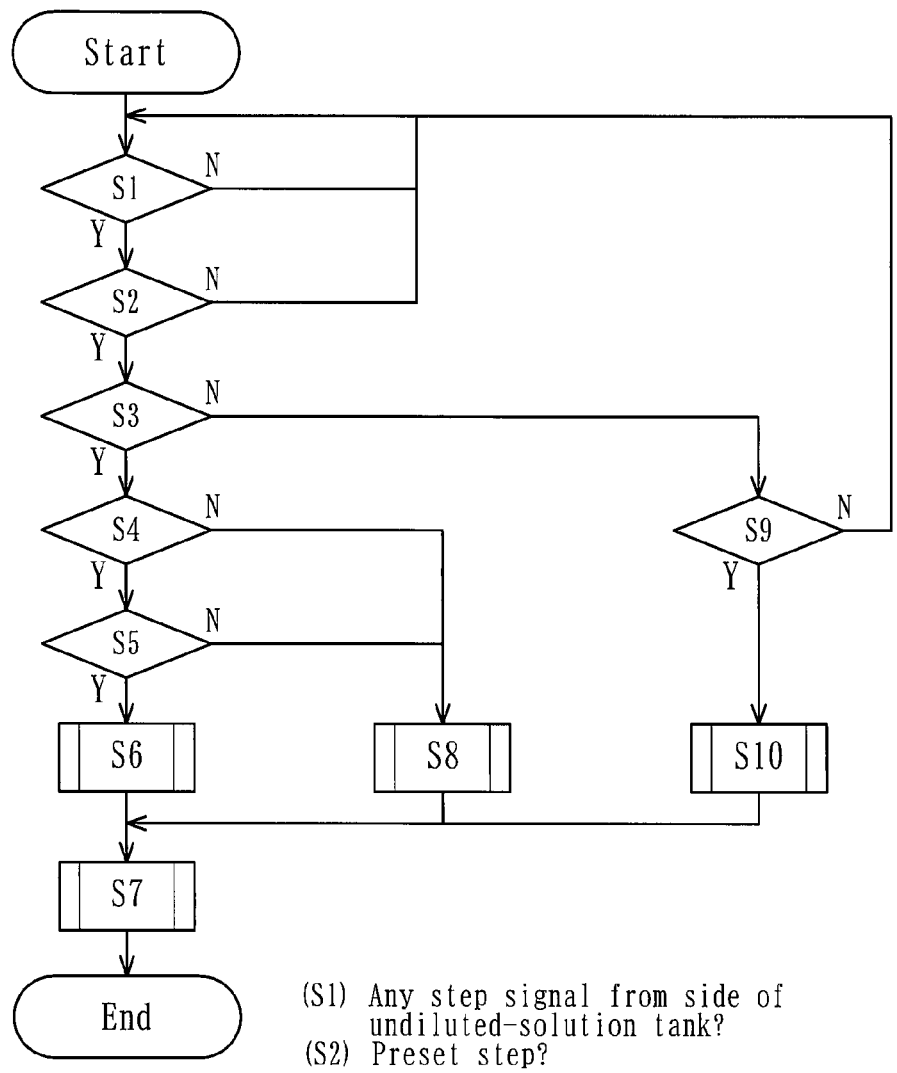

(S1) Any step signal from side of undiluted-solution tank?
(S2) Preset step?

(S3) Is A-solution tank under cleaning or disinfection?
(S4) Is B-solution tank under cleaning or disinfection?
(S5) Are disinfecting solutions the same?
(S6) Flushing steps with A and B (S7) Stand-alone cleaning step (S8) Flushing step for A-solution port (S9) Is B-solution tank under cleaning or disinfection?
(S10) Flushing step for B-solution port

BLOOD PURIFICATION APPARATUS

CROSS-REFERENCE TO RELATED APPLICATION(S)

This application is a continuation of International Application No. PCT/JP2020/020980 filed on May 27, 2020, which claims priority to Japanese Application No. 2019-099699, filed on May 28, 2019, the entire disclosures of which are hereby incorporated by reference.

FIELD

The present invention relates to a blood purification apparatus for giving blood purification treatment by purifying blood of a patient.

BACKGROUND

A dialysis apparatus serving as a blood purification apparatus intended for dialysis treatment or the like typically includes a line section through which dialysate to be introduced into a blood purifier or drain liquid discharged from the blood purifier is caused to flow, and a delivery unit that delivers liquid in the line section. Furthermore, a blood circuit through which blood of a patient is caused to extracorporeally circulate is connected to the blood purifier. While the blood of the patient is caused to extracorporeally circulate through the blood circuit, dialysis treatment (blood purification treatment) is performed with the blood purifier.

For example, a blood purification apparatus disclosed by PTL 1 includes an introduction port that allows dialysate flowing in a supply route to be introduced into the apparatus, an introduction route through which the dialysate introduced from the introduction port flows into a line section, and an electromagnetic valve capable of opening or closing the introduction route. To clean the supply route, a cleaning solution is caused to flow through a looped flow route provided near the introduction port, whereby the cleaning solution is caused to flow through the introduction route (particularly a portion of the introduction route that extends from the electromagnetic valve to the outside of the apparatus) for cleaning.

PTL 1: Japanese Unexamined Patent Application Publication No. 2005-124775 the teachings of which are expressly incorporated by reference herein for all purposes.

SUMMARY

In the above blood purification apparatus, however, the looped flow route for causing the cleaning solution flowing in the supply route to flow therethrough needs to be provided for cleaning the introduction route. Such a situation makes the configuration of the apparatus complicated. On the other hand, in a blood purification apparatus called personal dialysis apparatus, undiluted dialysate is caused to flow through a supply route and is diluted with clean water into working dialysate to be introduced into a blood purifier. In such an apparatus, if any undiluted dialysate remains in the introduction route, germs may propagate there. Hence, the introduction route needs to be cleaned and disinfected assuredly.

The present teachings have been conceived in view of the above circumstances and provides a blood purification apparatus in which an introduction route is cleaned and disinfected assuredly with a cleaning solution or a disinfecting solution flowing in a supply route, with no additional flow route.

According to the teachings of variation 1, there is provided a blood purification apparatus including a line section through which working dialysate to be introduced into a blood purifier or drain liquid discharged from the blood purifier is caused to flow; a delivery unit that delivers liquid in the line section; an introduction port connected to a supply route through which undiluted dialysate or the working dialysate is supplied, the introduction port allowing the undiluted dialysate or the working dialysate in the supply route to be introduced into the apparatus; an introduction route connected to the introduction port and through which the undiluted dialysate or the working dialysate introduced from the introduction port flows into the line section; a valve unit provided to the introduction route and being capable of opening or closing the introduction route by being opened or closed; and a control unit that controls an operation of opening or closing the valve unit. The control unit is capable of executing a flushing step in which when a cleaning solution or a disinfecting solution is caused to flow through the supply route, the valve unit is opened to allow the cleaning solution or the disinfecting solution flowing in the supply route to flow into the introduction route and through the line section to be discharged to an outside of the apparatus.

According to variation 2, in the blood purification apparatus according to variation 1, after the flushing step is ended, the control unit executes a stand-alone cleaning step in which the line section is cleaned with the valve unit closed.

According to variation 3, in the blood purification apparatus according to variation 1 or 2, the introduction route allows the undiluted dialysate flowing in the supply route to be introduced into the apparatus; the line section includes a dialysate introduction line into which clean water is introduced and in which the undiluted dialysate introduced from the introduction route is diluted with the clean water into the working dialysate, the working dialysate being introduced into the blood purifier through the dialysate introduction line, the line section further including a drain-liquid discharge line through which the drain liquid from the blood purifier is discharged; and when the flushing step is executed by the control unit, the cleaning solution or the disinfecting solution introduced from the introduction route is caused to flow through the dialysate introduction line and the drain-liquid discharge line.

According to variation 4, in the blood purification apparatus according to variation 3, the line section includes a bypass line connected to the dialysate introduction line and to the drain-liquid discharge line; and when the flushing step is executed by the control unit, the cleaning solution or the disinfecting solution introduced from the introduction route is caused to flow through the dialysate introduction line, the drain-liquid discharge line, and the bypass line.

According to variation 5, in the blood purification apparatus according to variation 3 or 4, the delivery unit is a duplex pump provided over the dialysate introduction line and the drain-liquid discharge line.

According to variation 6, in the blood purification apparatus according to any of variations 1 to 5, the introduction route is provided with an infusion pump that delivers the undiluted dialysate or the working dialysate introduced from the introduction port to the line section.

According to variation 7, in the blood purification apparatus according to any of variations 3 to 6, the undiluted dialysate includes an A-solution and a B-solution having different compositions to be generated into respective working dialysates; and the introduction port includes at least one of an A-solution introduction port that allows the A-solution flowing in the supply route to be introduced into the apparatus, and a B-solution introduction port that allows the B-solution flowing in the supply route to be introduced into the apparatus.

According to variation 8, in the blood purification apparatus according to variation 7, the introduction port includes the A-solution introduction port and the B-solution introduction port; and the control unit prohibits the introduction of the cleaning solution or the disinfecting solution from the B-solution introduction port while the cleaning solution or the disinfecting solution is being introduced from the A-solution introduction port, and prohibits the introduction of the cleaning solution or the disinfecting solution from the A-solution introduction port while the cleaning solution or the disinfecting solution is being introduced from the B-solution introduction port.

According to variation 9, in the blood purification apparatus according to any of variations 1 to 8, the control unit executes the flushing step if the blood purification apparatus is in a standby step as a standby state in which the line section is filled with clean water.

According to variation 10, in the blood purification apparatus according to any of variations 1 to 9, the control unit executes the flushing step if an operator performs a predetermined operation.

According to variation 11, in the blood purification apparatus according to any of variations 1 to 9, the control unit executes the flushing step automatically with reference to a start time or end time on a preset date.

According to variation 12, in the blood purification apparatus according to any of variations 1 to 9, the supply route is connected to an undiluted-solution tank containing the undiluted dialysate; and the control unit executes the flushing step with reference to a step signal received from a supply-side control unit that controls the undiluted-solution tank.

According to variation 1, the control unit is capable of executing the flushing step in which when the cleaning solution or the disinfecting solution is caused to flow through the supply route, the valve unit is opened to allow the cleaning solution or the disinfecting solution flowing in the supply route to flow into the introduction route and through the line section to be discharged to the outside of the apparatus. Therefore, the introduction route is cleaned and disinfected assuredly with the cleaning solution or the disinfecting solution flowing in the supply route, with no additional flow route.

According to variation 2, after the flushing step is ended, the control unit executes the stand-alone cleaning step in which the line section is cleaned with the valve unit closed. Therefore, the line section flushed with the cleaning solution or the disinfecting solution in the flushing step is cleaned in the stand-alone cleaning step. Consequently, subsequent blood purification treatment is performed under good conditions.

According to variation 3, when the flushing step is executed by the control unit, the cleaning solution or the disinfecting solution introduced from the introduction route is caused to flow through the dialysate introduction line and the drain-liquid discharge line. Therefore, the cleaning solution or the disinfecting solution introduced from the introduction route is discharged to the outside of the apparatus through the flow routes intended for blood purification treatment.

According to variation 4, the line section includes the bypass line connected to the dialysate introduction line and to the drain-liquid discharge line; and when the flushing step is executed by the control unit, the cleaning solution or the disinfecting solution introduced from the introduction route is caused to flow through the dialysate introduction line, the drain-liquid discharge line, and the bypass line. Therefore, the cleaning solution or the disinfecting solution introduced from the introduction route is discharged to the outside of the apparatus through the shortest route.

According to variation 5, the delivery unit is the duplex pump provided over the dialysate introduction line and the drain-liquid discharge line. Therefore, the cleaning solution or the disinfecting solution introduced from the introduction route is discharged to the outside of the apparatus by using the duplex pump, which is intended for blood purification treatment.

According to variation 6, the introduction route is provided with the infusion pump that delivers the undiluted dialysate or the working dialysate introduced from the introduction port to the line section. Therefore, in the flushing step, the cleaning solution or the disinfecting solution flowing in the supply route is caused to flow into the introduction route by using the infusion pump.

According to variation 7, the undiluted dialysate includes the A-solution and the B-solution having different compositions to be generated into the respective working dialysates; and the introduction port includes at least one of the A-solution introduction port that allows the A-solution flowing in the supply route to be introduced into the apparatus, and the B-solution introduction port that allows the B-solution flowing in the supply route to be introduced into the apparatus. Therefore, the A-solution or the B-solution is introduced into the apparatus assuredly and smoothly.

According to variation 8, the introduction port includes the A-solution introduction port and the B-solution introduction port; and the control unit prohibits the introduction of the cleaning solution or the disinfecting solution from the B-solution introduction port while the cleaning solution or the disinfecting solution is being introduced from the A-solution introduction port, and prohibits the introduction of the cleaning solution or the disinfecting solution from the A-solution introduction port while the cleaning solution or the disinfecting solution is being introduced from the B-solution introduction port. Such a configuration prevents the mixing between different cleaning solutions or disinfecting solutions in the line section that may be caused by simultaneous introduction of the different cleaning solutions or disinfecting solutions from the A-solution introduction port and the B-solution introduction port into the line section.

According to variation 9, the control unit executes the flushing step if the blood purification apparatus is in the standby step as the standby state in which the line section is filled with the clean water. Such a configuration prevents the mixing between any liquid other than the clean water, specifically the cleaning solution or the disinfecting solution, remaining in the line section and the cleaning solution or the disinfecting solution introduced from the introduction port into the line section.

According to variation 10, the control unit executes the flushing step if the operator performs the predetermined operation. Such a configuration prevents the execution of the flushing step with a wrong timing.

According to variation 11, the control unit executes the flushing step automatically with reference to the start time or end time on the preset date. Therefore, the flushing step is executed assuredly.

According to variation 12, the supply route is connected to the undiluted-solution tank containing the undiluted dialysate; and the control unit executes the flushing step with reference to the step signal received from the supply-side control unit that controls the undiluted-solution tank. Therefore, the flushing step is executed with an appropriate timing. Furthermore, the flushing step is executed assuredly and smoothly.

BRIEF DESCRIPTION OF THE DRAWINGS

FIG. 1 is a schematic diagram illustrating blood purification apparatuses and an undiluted-solution tank according to a first embodiment of the present invention.

FIG. 2 is a schematic diagram illustrating a line section of an apparatus body that is applied to each of the blood purification apparatuses.

FIG. 3 is a schematic diagram illustrating a blood circuit and a blood purifier applied to the blood purification apparatus.

FIG. 4 is a schematic diagram illustrating a display of the blood purification apparatus.

FIG. 5 is a flow chart illustrating a control sequence executed by a control unit of the blood purification apparatus.

FIG. 6 is a schematic diagram illustrating a route through which a cleaning solution or a disinfecting solution flows in a flushing step to be executed in the blood purification apparatus.

FIG. 7 is a schematic diagram illustrating blood purification apparatuses and undiluted-solution tanks according to a second embodiment of the present invention.

FIG. 8 is a flow chart illustrating a control sequence executed by a control unit of each of the blood purification apparatuses.

FIG. 9 is a flow chart illustrating another control sequence executed by the control unit of the blood purification apparatus.

FIG. 10 is a schematic diagram illustrating a route through which a cleaning solution or a disinfecting solution flows in a flushing step to be executed in the blood purification apparatus.

FIG. 11 is a flow chart illustrating a control sequence executed by a control unit of a blood purification apparatus according to a third embodiment of the present invention.

FIG. 12 is a flow chart illustrating a control sequence executed by a control unit of a blood purification apparatus according to a fourth embodiment of the present invention.

DETAILED DESCRIPTION

Embodiments of the present teachings will now be described specifically with reference to the drawings.

A blood purification apparatus according to an embodiment is applied to a hemodialysis apparatus 1 that performs dialysis treatment (blood purification treatment) by purifying blood of a patient that is caused to extracorporeally circulate. As illustrated in FIGS. 1 to 4, the blood purification apparatus includes a blood circuit 2 including an arterial blood circuit 2a and a venous blood circuit 2b; a dialyzer 3 serving as a blood purifier; an apparatus body including a line section, the line section including a dialysate introduction line L1, a drain-liquid discharge line L2, and so forth; a display M; and a control unit 13.

As illustrated in FIG. 3, the arterial blood circuit 2a is provided with a connector c at the distal end thereof. An arterial puncture needle (a) is connectable to the arterial blood circuit 2a through the connector c. Furthermore, a peristaltic blood pump 4 and an arterial air-trap chamber 5 are provided at respective halfway positions of the arterial blood circuit 2a. The venous blood circuit 2b is provided with a connector d at the distal end thereof. A venous puncture needle (b) is connectable to the venous blood circuit 2b through the connector d. Furthermore, a venous air-trap chamber 6 is provided at a halfway position of the venous blood circuit 2b. In the present embodiment, clamp units Va and Vb capable of closing or opening respective flow routes when opened or closed are provided to a distal portion (near the connector c) of the arterial blood circuit 2a and a distal portion (near the connector d) of the venous blood circuit 2b, respectively.

The dialyzer 3 (blood purifier) has, in a housing thereof, a blood inlet 3a (a blood introduction port), a blood outlet 3b (a blood delivery port), a dialysate inlet 3c (an inlet of a dialysate flow route, or a dialysate introduction port), and a dialysate outlet 3d (an outlet of the dialysate flow route, or a dialysate delivery port). The arterial blood circuit 2a is connected to the blood inlet 3a. The venous blood circuit 2b is connected to the blood outlet 3b. The dialysate inlet 3c and the dialysate outlet 3d are connected to the dialysate introduction line L1 and the drain-liquid discharge line L2, respectively.

The dialyzer 3 houses a plurality of hollow fiber membranes (not illustrated) formed of hollow fibers, serving as blood purification membranes for purifying the blood. The blood purification membranes in the dialyzer 3 define blood flow routes (each extending between the blood inlet 3a and the blood outlet 3b) through which the patient's blood flows and dialysate flow routes (each extending between the dialysate inlet 3c and the dialysate outlet 3d) through which dialysate flows. The hollow fiber membranes forming the blood purification membranes each have a number of microscopic holes (pores) extending therethrough from the outer peripheral surface to the inner peripheral surface. Impurities and the like contained in the blood are allowed to permeate through the membranes into the dialysate.

When the blood pump 4 is activated while the patient is punctured with the arterial puncture needle (a) connected to the distal end of the arterial blood circuit 2a and with the venous puncture needle (b) connected to the distal end of the venous blood circuit 2b, blood of the patient flows through the arterial blood circuit 2a while undergoing bubble removal in the arterial air-trap chamber 5 and reaches the dialyzer 3, where the blood is purified. Then, the blood flows through the venous blood circuit 2b while undergoing bubble removal in the venous air-trap chamber 6 and returns into the patient's body. Thus, the patient's blood is purified with the dialyzer 3 while being caused to extracorporeally circulate through the blood circuit 2 from the distal end of the arterial blood circuit 2a to the distal end of the venous blood circuit 2b.

On the other hand, the apparatus body includes the line section through which the dialysate to be introduced into the dialyzer 3 (blood purifier) or drain liquid discharged from the dialyzer 3 (blood purifier) is caused to flow, and a delivery unit that delivers liquid in the line section. As illustrated in FIG. 2, the line section includes the dialysate introduction line L1 through which the dialysate is introduced into the dialyzer 3, the drain-liquid discharge line L2 through which the drain liquid from the dialyzer 3 is discharged, a detour line L3 that detours a portion of the drain-liquid discharge line L2 where a duplex pump 7 is provided, and bypass lines (L4 and L5) each connected to the dialysate introduction line L1 and to the drain-liquid discharge line L2. The delivery unit is the duplex pump 7, which is provided over the dialysate introduction line L1 and the drain-liquid discharge line L2.

The dialysate introduction line L1 is provided with electromagnetic valves V1 and V3, filters F1 and F2, and mixing chambers 9 and 10. The dialysate introduction line L1 is supplied with clean water (RO water). An A-solution introduced from an A-solution introduction route La and a B-solution introduced from a B-solution introduction route Lb are each diluted with the clean water into a working dialysate at a predetermined concentration. The working dialysate thus generated is filtered by the filters F1 and F2 and is then introduced into the dialyzer 3.

The A-solution and the B-solution are solutions having different compositions for generating respective working dialysates. Specifically, the A-solution (an undiluted solution of A-material) is a mixed aqueous solution containing sodium chloride, potassium chloride, calcium chloride, magnesium chloride, sodium acetate, and the like. The B-solution (an undiluted solution of B-material) is an aqueous solution of sodium hydrogen carbonate. The A-solution and the B-solution are each introduced into and diluted in the dialysate introduction line L1 and are each stirred in a corresponding one of the mixing chambers 9 and 10, whereby a working dialysate having a uniform concentration is generated.

In the dialysate introduction line L1, the working dialysate to be introduced into the dialyzer 3 is filterable by the filters F1 and F2, and the flow route is closable or openable by the electromagnetic valves V1 and V3 with an arbitrary timing. The dialysate introduction line L1 is connected to the drain-liquid discharge line L2 through the bypass lines L4 and L5. The bypass lines L4 and L5 are provided with electromagnetic valves V5 and V6, respectively.

The drain-liquid discharge line L2 is provided with the detour line L3 that detours the duplex pump 7. The detour line L3 is provided with an ultrafiltration pump 8. Therefore, when the ultrafiltration pump 8 is activated in the process of causing the patient's blood to extracorporeally circulate through the blood circuit 2, ultrafiltration is performed in which water is removed from the blood flowing in the dialyzer 3.

The drain-liquid discharge line L2 is further provided with electromagnetic valves V2 and V4, which allow the drain liquid from the dialyzer 3 to be discharged to the outside. The drain-liquid discharge line L2 is further provided with flow routes L6 and L7 at respective positions on the upstream side (the right side in FIG. 2) with respect to the duplex pump 7. The flow route L6 is provided with an electromagnetic valve V9. The distal end of the flow route L6 is connected to a container m1 containing a cleaning solution. The flow route L7 is provided with an electromagnetic valve V10. The distal end of the flow route L7 is connected to a container m2 containing a disinfecting solution.

In FIG. 2, the distal end of the dialysate introduction line L1 and the distal end of the drain-liquid discharge line L2 are connected (short-circuited) to each other with a coupler C. To perform blood purification treatment, the coupler C is removed. Then, the distal end of the dialysate introduction line L1 is connected to the dialysate inlet 3c of the dialyzer 3, and the distal end of the drain-liquid discharge line L2 is connected to the dialysate outlet 3d of the dialyzer 3.

Blood purification apparatuses, denoted by 1, according to the present embodiment are connected to a supply route R (see FIG. 1) through which undiluted dialysate is supplied. The blood purification apparatuses 1 each include an introduction port (P1, P2) allowing the undiluted dialysate in the supply route (R, Ra) to be introduced into the apparatus, an introduction route (La, La1, La2, Lb, Lb1, Lb2) connected to the introduction port (P1, P2) and through which the undiluted dialysate introduced from the introduction port (P1, P2) flows into the line section (the dialysate introduction line L1), an electromagnetic valve (V7, V8) provided to the introduction route (La1, Lb1) and serving as a valve unit capable of opening or closing the introduction route (La1, Lb1) by being opened or closed, and a control unit 13 that controls an operation of opening or closing the electromagnetic valve (V7, V8) (the valve unit).

The introduction route (La1, Lb1) is a flow route connected to the dialysate introduction line L1 and provided for the introduction of the undiluted dialysate. In the present embodiment, the introduction route includes the A-solution introduction route La for the introduction of the A-solution, and the B-solution introduction route Lb for the introduction of the B-solution. The A-solution introduction route La includes an introduction route La1 provided with an A-solution infusion pump 11 and having the A-solution introduction port P1, and an introduction route La2 provided with a nozzle h1. The B-solution introduction route Lb includes an introduction route Lb1 provided with a B-solution infusion pump 12 and having the B-solution introduction port P2, and an introduction route Lb2 provided with a nozzle h2.

In a state where the nozzle h1 is fitted to a tank (not illustrated) containing the A-solution, when the A-solution infusion pump 11 is activated with the electromagnetic valve V7 (the valve unit) closed but with the electromagnetic valve V9 open, the A-solution in the tank having the nozzle h1 fitted thereto is delivered into the dialysate introduction line. In a state where the supply route (R, Ra) is connected to the A-solution introduction port P1, when the A-solution infusion pump 11 is activated with the electromagnetic valve V7 (the valve unit) open but with the electromagnetic valve V9 closed, the A-solution flowing in the supply route (R, Ra) is delivered into the dialysate introduction line.

Likewise, in a state where the nozzle h2 is fitted to a tank (not illustrated) containing the B-solution, when the B-solution infusion pump 12 is activated with the electromagnetic valve V8 (the valve unit) closed but with the electromagnetic valve V10 open, the B-solution in the tank having the nozzle h2 fitted thereto is delivered into the dialysate introduction line. In a state where the supply route (R, Ra) is connected to the B-solution introduction port P2, when the B-solution infusion pump 12 is activated with the electromagnetic valve V8 (the valve unit) open but with the electromagnetic valve V10 closed, the B-solution flowing in the supply route (R, Ra) is delivered into the dialysate introduction line.

In the present embodiment, the nozzle h1 is fitted to the tank containing the A-solution, and the supply route (R, Ra) is connected to the B-solution introduction port P2. As illustrated in FIG. 1, the supply route (R, Ra) includes a header R connected to an undiluted-solution tank T containing the undiluted dialysate (in the present embodiment, the B-solution), and branch lines Ra extending from the header R to the respective blood purification apparatuses 1 and connected to the respective B-solution introduction ports P2.

The set of the header R and the branch lines Ra corresponds to the "supply route" according to the present invention.

In the above configuration, the dialysate introduction line L1 according to the present embodiment receives the A-solution from the tank attached to the blood purification apparatus 1 and also receives the B-solution from the supply route (R, Ra), and each of the two solutions is diluted with the clean water (RO water) into a working dialysate. Note that a plurality of blood purification apparatuses 1 are installed in a dialysis room of a medical facility, and each of the blood purification apparatuses 1 is supplied with the B-solution through the supply route (R, Ra).

The control unit 13 is a microcomputer or the like provided on the apparatus body and is capable of executing a flushing step in which when the cleaning solution (for example, the clean water (RO water)) or the disinfecting solution (for example, a disinfecting solution based on acid such as citric acid, peracetic acid, or acetic acid or a disinfecting solution based on chlorine such as sodium hypochlorite) is caused to flow through the supply route (R, Ra), as illustrated in FIG. 6, the electromagnetic valve V8 (the valve unit) is opened to allow the cleaning solution or the disinfecting solution flowing in the supply route (R, Ra) to flow into the B-solution introduction route (Lb, Lb1) and through the line section (the dialysate introduction line L1, the drain-liquid discharge line L2, and the bypass line L4) to be discharged to the outside of the apparatus.

The control unit 13 according to the present embodiment executes the flushing step if the blood purification apparatus 1 is in a standby step as a standby state in which the line section is filled with the clean water (RO water). The standby step is a state established after the dialysis treatment is ended or with any other like timing. In the standby step, the lines included in the blood purification apparatus 1 are filled with the clean water, and the actuators included in the blood purification apparatus 1 are stopped. Normally, the standby step, a preparation step, a blood purification treatment step, a cleaning step, the standby step, and the preparation step are executed in that order.

The control unit 13 according to the present embodiment executes the flushing step if an operator performs a predetermined operation. Specifically, the blood purification apparatus 1 includes the display M, which is a touch panel. As illustrated in FIG. 4, the display M has a log-displaying portion Ma, an operating portion Mb, an operating portion Mc, and a duration-displaying portion Md. The log-displaying portion Ma provides a log summarizing the start and end of the flushing step for the A-solution introduction route (La, La1) and the flushing step for the B-solution introduction route (Lb, Lb1). In the present embodiment, the log displayed includes the duration of the flushing step. The duration-displaying portion Md provides the current duration during the flushing step. While the flushing step is stopped, an indication "---" is displayed, for example.

The operating portion Mb serves as an operating portion with which the flushing step for the A-solution introduction route (La, La1) is started or ended. When the operator makes an input by touching the operating portion Mb while the flushing step is stopped, the flushing step for the A-solution introduction route (La, La1) is started. When the operator makes an input by touching the operating portion Mb while the flushing step is in progress, the flushing step for the A-solution introduction route (La, La1) is ended.

The operating portion Mc serves as an operating portion with which the flushing step for the B-solution introduction route (Lb, Lb1) is started or ended. When the operator makes an input by touching the operating portion Mc while the flushing step is stopped, the flushing step for the B-solution introduction route (Lb, Lb1) is started. When the operator makes an input by touching the operating portion Mc while the flushing step is in progress, the flushing step for the B-solution introduction route (Lb, Lb1) is ended. The operating portion Mb and the operating portion Mc may be integrated into one operating portion. In that case, the one operating portion (Mb, Mc) may be configured such that an operation on the operating portion (Mb, Mc) changes the screen displayed on the display M to a screen for selecting one of the A-solution and the B-solution.

The control unit 13 according to the present embodiment further executes a stand-alone cleaning step after the flushing step is ended. In the stand-alone cleaning step, the line section is cleaned with the valve unit (in the present embodiment, the electromagnetic valve V8) closed. The stand-alone cleaning step is a step of cleaning or disinfecting the lines included in the blood purification apparatus 1. In the stand-alone cleaning step, the cleaning solution in the container m1 or the disinfecting solution in the container m2 is caused to flow through the lines by activating the duplex pump 7 while the introduction of the cleaning solution or the disinfecting solution from the supply route (R, Ra) is stopped.

Now, a control sequence executed by the control unit 13 according to the present embodiment will be described with reference to a flow chart illustrated in FIG. 5.

First, it is confirmed that the cleaning solution or the disinfecting solution is flowing in the supply route (R, Ra). Then, in S1, it is determined whether an operation of starting flushing is performed with the operator's input operation (a touching operation) on the operating portion Mc of the display M. If it is determined that the operation of starting flushing is performed, the sequence proceeds to S2, in which it is determined whether the blood purification apparatus 1 is in the standby step.

In S2, if it is determined that the blood purification apparatus 1 is in the standby step, the sequence proceeds to S3, in which the flushing step is executed. In the flushing step, as illustrated in FIG. 6, the electromagnetic valves V8, V5, and V4 are open, and the duplex pump 7 and the B-solution infusion pump 12 are activated. Accordingly, the cleaning solution or the disinfecting solution flowing in the supply route (R, Ra) is introduced into the B-solution introduction route (Lb, Lb1), flows through relevant lines (the dialysate introduction line L1, the bypass line L4, and the drain-liquid discharge line L2) illustrated by bold lines in FIG. 6, and is discharged to the outside of the apparatus.

Subsequently, in S4, it is determined whether an operation of ending flushing is performed with the operator's input operation (a touching operation) on the operating portion Mc of the display M. If it is determined that the operation of ending flushing is performed, the sequence proceeds to S5, in which it is determined whether an operation of starting the stand-alone cleaning step is performed. In S5, if it is determined that the operation of starting the stand-alone cleaning step is performed, the sequence proceeds to S6, in which the stand-alone cleaning step is executed. In the stand-alone cleaning step, as described above, the cleaning solution in the container m1 or the disinfecting solution in the container m2 is caused to flow through relevant lines with the electromagnetic valve V8 (the valve unit) closed to stop the introduction of the cleaning solution or the disinfecting solution from the supply route (R, Ra), whereby the lines of the blood purification apparatus 1 are cleaned or disinfected.

When the stand-alone cleaning step ends, the control sequence ends. If it is not determined in S1 that the operation of starting flushing is performed, S1 is repeated. If it is not determined in S2 that the blood purification apparatus 1 is in the standby step, the sequence returns to S1. If it is not determined in S4 that the operation of ending flushing is performed, the sequence returns to S3. If it is not determined in S5 that the operation of starting the stand-alone cleaning step is performed, S5 is repeated. In the present embodiment, the stand-alone cleaning step is controlled to be executed only if the operation of starting the stand-alone cleaning step is performed. Alternatively, the stand-alone cleaning step may be preset to be executed automatically after the flushing step.

Now, a blood purification apparatus according to a second embodiment of the present invention will be described.

As with the case of the first embodiment, a blood purification apparatus 1 according to the present embodiment is applied to a hemodialysis apparatus 1 that performs dialysis treatment (blood purification treatment) by purifying blood of a patient that is caused to extracorporeally circulate. As illustrated in FIGS. 2 and 3, the blood purification apparatus includes a blood circuit 2 including an arterial blood circuit 2a and a venous blood circuit 2b; a dialyzer 3 serving as a blood purifier; an apparatus body including a line section, the line section including a dialysate introduction line L1, a drain-liquid discharge line L2, and so forth; a display M; and a control unit 13. Elements that are the same as those described in the first embodiment are denoted by corresponding ones of the reference signs, and detailed description of those elements is omitted.

In the present embodiment, the electromagnetic valve V9 provided to the A-solution introduction route La2 and the electromagnetic valve V10 provided to the B-solution introduction route Lb2 are closed. Furthermore, as illustrated in FIG. 7, a supply route (R1, R1a) is connected to the A-solution introduction port P1, and another supply route (R2, R2a) is connected to the B-solution introduction port P2. The supply route (R1, R1a) includes a header R1 connected to an undiluted-solution tank T1 containing the A-solution, and branch lines R1a extending from the header R1 to the respective blood purification apparatuses 1 and connected to the respective A-solution introduction ports P1. The other supply route (R2, R2a) includes a header R2 connected to an undiluted-solution tank T2 containing the B-solution, and branch lines R2a extending from the header R2 to the respective blood purification apparatuses 1 and connected to the respective B-solution introduction ports P2.

In the above configuration, the dialysate introduction line L1 according to the present embodiment receives the A-solution from the supply route (R1, R1a) and also receives the B-solution from the supply route (R2, R2a). Each of the two solutions is diluted with the clean water (RO water) into a working dialysate. Note that a plurality of blood purification apparatuses 1 are installed in a dialysis room of a medical facility, and each of the blood purification apparatuses 1 is supplied with the A-solution and the B-solution through the respective supply routes (R1, R1a) (R2, R2a).

The control unit 13 is a microcomputer or the like provided on the apparatus body and is capable of executing a flushing step in which when the cleaning solution or the disinfecting solution is caused to flow through the supply route (R2, R2a), as illustrated in FIG. 6, the electromagnetic valve V8 (the valve unit) is opened to allow the cleaning solution or the disinfecting solution flowing in the supply route (R2, R2a) to flow into the B-solution introduction route (Lb, Lb1) and through the line section (the dialysate introduction line L1, the drain-liquid discharge line L2, and the bypass line L4) to be discharged to the outside of the apparatus; and a flushing step in which when the cleaning solution or the disinfecting solution is caused to flow through the supply route (R1, R1a), as illustrated in FIG. 10, the electromagnetic valve V7 (the valve unit) is opened to allow the cleaning solution or the disinfecting solution flowing in the supply route (R1, R1a) to flow into the A-solution introduction route (La, La1) and through the line section (the dialysate introduction line L1, the drain-liquid discharge line L2, and the bypass line L4) to be discharged to the outside of the apparatus.

As with the case of the first embodiment, the control unit 13 according to the present embodiment executes the flushing steps (in the present embodiment, the flushing step with the A-solution and the flushing step with the B-solution) if the blood purification apparatus 1 is in the standby step as the standby state in which the line section is filled with the clean water (RO water). Furthermore, as with the case of the first embodiment, the control unit 13 according to the present embodiment executes each of the flushing steps if the operator performs a predetermined operation (an operation performed on a corresponding one of the operating portions Mb and Mc of the display M).

The control unit 13 according to the present embodiment operates as follows. While the cleaning solution or the disinfecting solution is being introduced from the A-solution introduction port P1, the control unit 13 prohibits the introduction of the cleaning solution or the disinfecting solution from the B-solution introduction port P2. Furthermore, while the cleaning solution or the disinfecting solution is being introduced from the B-solution introduction port P2, the control unit 13 prohibits the introduction of the cleaning solution or the disinfecting solution from the A-solution introduction port P1. In such a control operation, the cleaning solution or the disinfecting solution is prevented from being introduced into the lines of the apparatus from the A-solution introduction port P1 and from the B-solution introduction port P2.

Now, a control sequence (the flushing step for the B-solution) executed by the control unit 13 according to the present embodiment will be described with reference to a flow chart illustrated in FIG. 8.

First, it is confirmed that the cleaning solution or the disinfecting solution is flowing in the supply route (R2, R2a). Then, in S1, it is determined whether an operation of starting flushing for the B-solution is performed with the operator's input operation (a touching operation) on the operating portion Mc of the display M. If it is determined that the operation of starting flushing for the B-solution is performed, the sequence proceeds to S2, in which it is determined whether the flushing step for the A-solution (a step of introducing the cleaning solution or the disinfecting solution from the A-solution introduction port P1) is stopped.

If it is determined in S2 that the flushing step for the A-solution is stopped, the sequence proceeds to S3, in which it is determined whether the blood purification apparatus 1 is in the standby step. If it if determined in S3 that the blood purification apparatus 1 is in the standby step, the sequence proceeds to S4, in which the flushing step for the B-solution is executed. In the flushing step for the B-solution, as illustrated in FIG. 6, the electromagnetic valves V8, V5, and V4 are open, and the duplex pump 7 and the B-solution infusion pump 12 are activated. Accordingly, the cleaning solution or the disinfecting solution flowing in the supply route (R2, R2a) is introduced into the B-solution introduction route (Lb, Lb1), flows through relevant lines (the dialysate introduction line L1, the bypass line L4, and the drain-liquid discharge line L2) illustrated by bold lines in FIG. 6, and is discharged to the outside of the apparatus.

Subsequently, in S5, it is determined whether an operation of ending flushing for the B-solution is performed with the operator's input operation (a touching operation) on the operating portion Mc of the display M. If it is determined that the operation of ending flushing for the B-solution is performed, the sequence proceeds to S6, in which it is determined whether an operation of starting the stand-alone cleaning step is performed. In S6, if it is determined that the operation of starting the stand-alone cleaning step is performed, the sequence proceeds to S7, in which the stand-alone cleaning step is executed. In the stand-alone cleaning step, as described above, the cleaning solution in the container m1 or the disinfecting solution in the container m2 is caused to flow through relevant lines with the electromagnetic valve V8 (the valve unit) and the electromagnetic valve V7 (the valve unit) closed to stop the introduction of the cleaning solution or the disinfecting solution from the supply route (R1, R1a) (R2, R2a), whereby the lines of the blood purification apparatus 1 are cleaned or disinfected.

When the stand-alone cleaning step ends, the control sequence ends. If it is not determined in S1 that the operation of starting flushing for the B-solution is performed, S1 is repeated. If it is not determined in S2 that the flushing step for the A-solution is stopped or if it is not determined in S3 that the blood purification apparatus 1 is in the standby step, the sequence returns to S1. If it is not determined in S5 that the operation of ending flushing for the B-solution is performed, the sequence returns to S4. If it is not determined in S6 that the operation of starting the stand-alone cleaning step is performed, S6 is repeated. In the present embodiment, the stand-alone cleaning step is controlled to be executed only if the operation of starting the stand-alone cleaning step is performed. Alternatively, the stand-alone cleaning step may be preset to be executed automatically after the flushing step.

Now, another control sequence (the flushing step for the A-solution) executed by the control unit 13 according to the present embodiment will be described with reference to a flow chart illustrated in FIG. 9.

First, it is confirmed that the cleaning solution or the disinfecting solution is flowing in the supply route (R1, R1a). Then, in S1, it is determined whether an operation of starting flushing for the A-solution is performed with the operator's input operation (a touching operation) on the operating portion Mb of the display M. If it is determined that the operation of starting flushing for the A-solution is performed, the sequence proceeds to S2, in which it is determined whether the flushing step for the B-solution (a step of introducing the cleaning solution or the disinfecting solution from the B-solution introduction port P2) is stopped.

If it is determined in S2 that the flushing step for the B-solution is stopped, the sequence proceeds to S3, in which it is determined whether the blood purification apparatus 1 is in the standby step. If it if determined in S3 that the blood purification apparatus 1 is in the standby step, the sequence proceeds to S4, in which the flushing step for the A-solution is executed. In the flushing step for the A-solution, as illustrated in FIG. 10, the electromagnetic valves V7, V5, and V4 are opened, and the duplex pump 7 and the A-solution infusion pump 11 are activated. Accordingly, the cleaning solution or the disinfecting solution flowing in the supply route (R1, R1a) is introduced into the A-solution introduction route (La, La1), flows through relevant lines (the dialysate introduction line L1, the bypass line L4, and the drain-liquid discharge line L2) illustrated by bold lines in FIG. 10, and is discharged to the outside of the apparatus.

Subsequently, in S5, it is determined whether an operation of ending flushing for the A-solution is performed with the operator's input operation (a touching operation) on the operating portion Mb of the display M. If it is determined that the operation of ending flushing for the A-solution is performed, the sequence proceeds to S6, in which it is determined whether an operation of starting the stand-alone cleaning step is performed. In S6, if it is determined that the operation of starting the stand-alone cleaning step is performed, the sequence proceeds to S7, in which the stand-alone cleaning step is executed. In the stand-alone cleaning step, as described above, the cleaning solution in the container m1 or the disinfecting solution in the container m2 is caused to flow through relevant lines with the electromagnetic valve V8 (the valve unit) and the electromagnetic valve V7 (the valve unit) closed to stop the introduction of the cleaning solution or the disinfecting solution from the supply route (R1, R1a) (R2, R2a), whereby the lines of the blood purification apparatus 1 are cleaned or disinfected.

When the stand-alone cleaning step ends, the control sequence ends. If it is not determined in S1 that the operation of starting flushing for the A-solution is performed, S1 is repeated. If it is not determined in S2 that the flushing step for the B-solution is stopped or if it is not determined in S3 that the blood purification apparatus 1 is in the standby step, the sequence returns to S1. If it is not determined in S5 that the operation of ending flushing for the A-solution is performed, the sequence returns to S4. If it is not determined in S6 that the operation of starting the stand-alone cleaning step is performed, S6 is repeated. In the present embodiment, the stand-alone cleaning step is controlled to be executed only if the operation of starting the stand-alone cleaning step is performed. Alternatively, the stand-alone cleaning step may be preset to be executed automatically after the flushing step.

Now, a blood purification apparatus according to a third embodiment of the present teachings will be described.

As with the cases of the first and second embodiments, a blood purification apparatus 1 according to the present embodiment is applied to a hemodialysis apparatus 1 that performs dialysis treatment (blood purification treatment) by purifying blood of a patient that is caused to extracorporeally circulate. As illustrated in FIGS. 2 and 3, the blood purification apparatus includes a blood circuit 2 including an arterial blood circuit 2a and a venous blood circuit 2b; a dialyzer 3 serving as a blood purifier; an apparatus body including a line section, the line section including a dialysate introduction line L1, a drain-liquid discharge line L2, and so forth; a display M; and a control unit 13. Elements that are the same as those described in the first and second embodiments are denoted by corresponding ones of the reference signs, and detailed description of those elements is omitted.

In the present embodiment, as with the case of the first embodiment, the nozzle h1 is fitted to the tank containing the A-solution, and the supply route (R, Ra) is connected to the B-solution introduction port P2. As illustrated in FIG. 1, the supply route (R, Ra) includes the header R connected to the undiluted-solution tank T containing the undiluted dialysate (in the present embodiment, the B-solution), and the branch lines Ra extending from the header R to the respective blood purification apparatuses 1 and connected to the respective B-solution introduction ports P2.

In the above configuration, the dialysate introduction line L1 according to the present embodiment receives the A-solution from the tank attached to the blood purification apparatus 1 and also receives the B-solution from the supply route (R, Ra), and each of the two solutions is diluted with the clean water (RO water) into a working dialysate. Note that a plurality of blood purification apparatuses 1 are installed in a dialysis room of a medical facility, and each of the blood purification apparatuses 1 is supplied with the B-solution through the supply route (R, Ra).

The control unit 13 is a microcomputer or the like provided on the apparatus body and is capable of executing a flushing step in which when the cleaning solution or the disinfecting solution is caused to flow through the supply route (R, Ra), as illustrated in FIG. 6, the electromagnetic valve V8 (the valve unit) is opened to allow the cleaning solution or the disinfecting solution flowing in the supply route (R, Ra) to flow into the B-solution introduction route (Lb, Lb1) and through the line section (the dialysate introduction line L1, the drain-liquid discharge line L2, and the bypass line L4) to be discharged to the outside of the apparatus.

The control unit 13 according to the present embodiment executes the flushing step if the blood purification apparatus 1 is in the standby step as the standby state in which the line section is filled with the clean water (RO water). The standby step is a state established after the dialysis treatment is ended or with any other like timing. In the standby step, the lines included in the blood purification apparatus 1 are filled with the clean water, and the actuators included in the blood purification apparatus 1 are stopped. Normally, the standby step, the preparation step, the blood purification treatment step, the cleaning step, the standby step, and the preparation step are executed in that order.

The control unit 13 according to the present embodiment further executes the stand-alone cleaning step after the flushing step is ended. In the stand-alone cleaning step, the line section is cleaned with the valve unit (in the present embodiment, the electromagnetic valve V8) closed. The stand-alone cleaning step is a step of cleaning or disinfecting the lines included in the blood purification apparatus 1. In the stand-alone cleaning step, the cleaning solution in the container m1 or the disinfecting solution in the container m2 is caused to flow through the lines by activating the duplex pump 7 while the introduction of the cleaning solution or the disinfecting solution from the supply route (R, Ra) is stopped.

In particular, the control unit 13 according to the present embodiment automatically executes the flushing step with reference to the start time or end time on a preset date. Specifically, with reference to a schedule (timetable) for cleaning or disinfection of the supply route (R, Ra), a date or day of the week and a start time or end time for the execution of the flushing step are inputted to the blood purification apparatus 1 in advance, so that the flushing step is controlled to be started at the inputted start time on the inputted date or day of the week and to be ended at the inputted end time.

Alternatively, the flushing step may be automatically executed by presetting the duration of the flushing step, as well as the date, the start time, and the end time. Furthermore, for example, the stand-alone cleaning step may be automatically executed by presetting the type and duration of cleaning to be performed. In the present embodiment, the flushing step for the B-solution is controlled to be automatically executed at the reaching of the start time on the preset date. If both the flushing step for the A-solution and the flushing step for the B-solution are executable as in the second embodiment, whether to start the flushing step for the A-solution or the flushing step for the B-solution may be set in advance for automatic execution.

Now, a control sequence executed by the control unit 13 according to the present embodiment will be described with reference to a flow chart illustrated in FIG. 11.

First, it is confirmed that the cleaning solution or the disinfecting solution is flowing in the supply route (R, Ra). Then, in S1, it is determined whether the present date and time is the preset date and time (start time). If it is determined that the present date and time is the preset date and time (start time), the sequence proceeds to S2, in which it is determined whether the blood purification apparatus 1 is in the standby step.

In S2, if it is determined that the blood purification apparatus 1 is in the standby step, the sequence proceeds to S3, in which the flushing step is executed. In the flushing step, as illustrated in FIG. 6, the electromagnetic valves V8, V5, and V4 are open, and the duplex pump 7 and the B-solution infusion pump 12 are activated. Accordingly, the cleaning solution or the disinfecting solution flowing in the supply route (R, Ra) is introduced into the B-solution introduction route (Lb, Lb1), flows through relevant lines (the dialysate introduction line L1, the bypass line L4, and the drain-liquid discharge line L2) illustrated by bold lines in FIG. 6, and is discharged to the outside of the apparatus.

After the flushing step is executed as above, the stand-alone cleaning step is executed in S4. In the stand-alone cleaning step, as described above, the cleaning solution in the container m1 or the disinfecting solution in the container m2 is caused to flow through relevant lines with the electromagnetic valve V8 (the valve unit) closed to stop the introduction of the cleaning solution or the disinfecting solution from the supply route (R, Ra), whereby the lines of the blood purification apparatus 1 are cleaned or disinfected.

When the stand-alone cleaning step ends, the control sequence ends. If it is not determined in S1 that the present date and time is the preset date and time (start time), S1 is repeated. If it is not determined in S2 that the blood purification apparatus 1 is in the standby step, the sequence returns to S1. It is not necessary to automatically start or end the stand-alone cleaning step in accordance with a program setting as described in the present embodiment. The stand-alone cleaning step may be started or ended with an operator's starting operation.

Now, a blood purification apparatus according to a fourth embodiment of the present teachings will be described.

As with the cases of the first to third embodiments, a blood purification apparatus 1 according to the present embodiment is applied to a hemodialysis apparatus 1 that performs dialysis treatment (blood purification treatment) by purifying blood of a patient that is caused to extracorporeally circulate. As illustrated in FIGS. 2 and 3, the blood purification apparatus includes a blood circuit 2 including an arterial blood circuit 2a and a venous blood circuit 2b; a dialyzer 3 serving as a blood purifier; an apparatus body including a line section, the line section including a dialysate introduction line L1, a drain-liquid discharge line L2, and so forth; a display M; and a control unit 13. Elements that are the same as those described in the first to third embodiments are denoted by corresponding ones of the reference signs, and detailed description of those elements is omitted.

In the present embodiment, as with the case of the second embodiment, the electromagnetic valve V9 provided to the A-solution introduction route La2 and the electromagnetic valve V10 provided to the B-solution introduction route Lb2 are closed. Furthermore, as illustrated in FIG. 7, the supply route (R1, R1a) is connected to the A-solution introduction port P1, and the other supply route (R2, R2a) is connected to the B-solution introduction port P2. The supply route (R1, R1a) includes the header R1 connected to the undiluted-solution tank T1 containing the A-solution, and the branch lines R1a extending from the header R1 to the respective blood purification apparatuses 1 and connected to the respective A-solution introduction ports P1. The other supply route (R2, R2a) includes the header R2 connected to the undiluted-solution tank T2 containing the B-solution, and the branch lines R2a extending from the header R2 to the respective blood purification apparatuses 1 and connected to the respective B-solution introduction ports P2.

In the above configuration, the dialysate introduction line L1 according to the present embodiment receives the A-solution from the supply route (R1, R1a) and also receives the B-solution from the supply route (R2, R2a). Each of the two solutions is diluted with the clean water (RO water) into a working dialysate. Note that a plurality of blood purification apparatuses 1 are installed in a dialysis room of a medical facility, and each of the blood purification apparatuses 1 is supplied with the A-solution and the B-solution through the respective supply routes (R1, R1a) (R2, R2a).

The control unit 13 is a microcomputer or the like provided on the apparatus body and is capable of executing the flushing step in which when the cleaning solution or the disinfecting solution is caused to flow through the supply route (R2, R2a), as illustrated in FIG. 6, the electromagnetic valve V8 (the valve unit) is opened to allow the cleaning solution or the disinfecting solution flowing in the supply route (R2, R2a) to flow into the B-solution introduction route (Lb, Lb1) and through the line section (the dialysate introduction line L1, the drain-liquid discharge line L2, and the bypass line L4) to be discharged to the outside of the apparatus; and the flushing step in which when the cleaning solution or the disinfecting solution is caused to flow through the supply route (R1, R1a), as illustrated in FIG. 10, the electromagnetic valve V7 (the valve unit) is opened to allow the cleaning solution or the disinfecting solution flowing in the supply route (R1, R1a) to flow into the A-solution introduction route (La, La1) and through the line section (the dialysate introduction line L1, the drain-liquid discharge line L2, and the bypass line L4) to be discharged to the outside of the apparatus.

As with the cases of the first to third embodiments, the control unit 13 according to the present embodiment executes the flushing steps (in the present embodiment, the flushing step with the A-solution and the flushing step with the B-solution) if the blood purification apparatus 1 is in the standby step as the standby state in which the line section is filled with the clean water (RO water). As with the cases of the first and second embodiments, the control unit 13 according to the present embodiment executes each of the flushing steps if the operator performs a predetermined operation (an operation performed on a corresponding one of the operating portions Mb and Mc of the display M).

The control unit 13 according to the present embodiment receives a step signal from a supply-side control unit (not illustrated) that controls the undiluted-solution tanks (T1, T2). With reference to the step signal, the control unit 13 executes the flushing step. The step signal received from the supply-side control unit is any of signals for the following steps: an undiluted-solution-supplying step in which the undiluted solution is supplied, a cleaning step with RO water, a disinfecting step with a chlorinated disinfecting solution, a disinfecting step with an acidic disinfecting solution, and the like.

Now, a control sequence executed by the control unit 13 according to the present embodiment will be described with reference to a flow chart illustrated in FIG. 12.

First, in S1, it is determined whether any step signal (for the cleaning step with RO water, the disinfecting step with a chlorinated disinfecting solution, the disinfecting step with an acidic disinfecting solution, or the like) from the supply-side control unit is received by the blood purification apparatus 1. If it is determined that any step signal is received, the sequence proceeds to S2, in which it is determined whether the blood purification apparatus 1 is in the standby step.

In S2, if it is determined that the blood purification apparatus 1 is in the standby step, the sequence proceeds to S3, in which it is determined whether the side of the A-solution tank T1 (the tank T1 and the supply route (R1, R1a)) is in the cleaning or disinfecting step. If it is determined that the side of the A-solution tank T1 is in the cleaning or disinfecting step, the sequence proceeds to S4, in which it is determined whether the side of the B-solution tank T2 (the tank T2 and the supply route (R2, R2a)) is in the cleaning or disinfecting step.

Subsequently, if it is determined in S4 that the side of the B-solution tank T2 is in the cleaning or disinfecting step, the sequence proceeds to S5, in which it is determined whether the disinfecting solution to be used in the disinfecting step for the side of the A-solution tank T1 and the disinfecting solution to be used in the disinfecting step for the side of the B-solution tank are the same. If it is determined in S5 that the disinfecting solution to be used in the disinfecting step for the side of the A-solution tank T1 and the disinfecting solution to be used in the disinfecting step for the side of the B-solution tank are the same, the sequence proceeds to S6, in which the flushing step with the A-solution and the flushing step with the B-solution are executed by opening the electromagnetic valves V7 and V8 as the valve unit according to the present invention to allow the introduction of the A-solution and the B-solution from the A-solution introduction port P1 and the B-solution introduction port P2, respectively.

If it is not determined in S4 that the side of the B-solution tank T2 is in the cleaning or disinfecting step, the sequence proceeds to S8, in which the flushing step with the A-solution is executed by opening the electromagnetic valve V7 as the valve unit according to the present teachings to allow the introduction of the A-solution from the A-solution introduction port P1. On the other hand, if it is not determined in S3 that the side of the A-solution tank T1 is in the cleaning or disinfecting step, the sequence proceeds to S9, in which it is determined whether the side of the B-solution tank T2 (the tank T2 and the supply route (R2, R2a)) is in the cleaning or disinfecting step. If it is determined in S9 that the side of the B-solution tank T2 is in the cleaning or disinfecting step, the sequence proceeds to S10, in which the flushing step with the B-solution is executed by opening the electromagnetic valve V8 as the valve unit according to the present invention to allow the introduction of the B-solution from the B-solution introduction port P2.

After any of the flushing steps is executed as above, the stand-alone cleaning step is executed in S7. In the stand-alone cleaning step, as described above, the cleaning solution in the container m1 or the disinfecting solution in the container m2 is caused to flow through relevant lines with the electromagnetic valves V7 and V8 (the valve units) closed to stop the introduction of the cleaning solution or the disinfecting solution from the supply route (R1, R1a) (R2, R2a), whereby the lines of the blood purification apparatus 1 are cleaned or disinfected.

When the stand-alone cleaning step ends, the control sequence ends. If it is not determined in S1 that any step signal (for the cleaning step with RO water, the disinfecting step with a chlorinated disinfecting solution, the disinfecting step with an acidic disinfecting solution, or the like) from the supply-side control unit is received by the blood purification apparatus 1, S1 is repeated. If it is not determined in S2 that the blood purification apparatus 1 is in the standby step, the sequence returns to S1. It is not necessary to automatically start or end the stand-alone cleaning step in accordance with a program setting as described in the present embodiment. The stand-alone cleaning step may be started or ended with an operator's starting operation.

In the present embodiment, which of the flushing step with the A-solution and the flushing step with the B-solution is to be executed is automatically determined. Alternatively, which of the flushing step with the A-solution and the flushing step with the B-solution is to be executed may be determined if the operator performs a certain operation. Furthermore, if it is not determined in S5 that the disinfecting solution to be used in the disinfecting step for the side of the A-solution tank T1 and the disinfecting solution to be used in the disinfecting step for the side of the B-solution tank are the same, the flushing step with the A-solution is executed in S8. Alternatively, the flushing step with the B-solution may be executed in S8.

According to each of the first to fourth embodiments, the control unit 13 is capable of executing the flushing step in which when the cleaning solution or the disinfecting solution is caused to flow through the supply route (R, Ra, R1, R1a, R2, R2a), the electromagnetic valve (V7 or V8) (the valve unit) is opened to allow the cleaning solution or the disinfecting solution flowing in the supply route (R, Ra, R1, R1a, R2, R2a) to flow into the introduction route (the A-solution introduction route La, La1 or the B-solution introduction route Lb, Lb1) and through the line section to be discharged to the outside of the apparatus. Therefore, the introduction route (the A-solution introduction route La, La1 or the B-solution introduction route Lb, Lb1) is cleaned and disinfected assuredly with the cleaning solution or the disinfecting solution flowing in the supply route (R, Ra, R1, R1a, R2, R2a), with no additional flow route.

The control unit 13 according to each of the first to fourth embodiments executes the stand-alone cleaning step after the flushing step is ended. In the stand-alone cleaning step, the line section is cleaned with the electromagnetic valve (V7 or V8) (the valve unit) closed. Therefore, the line section flushed with the cleaning solution or the disinfecting solution in the flushing step is cleaned in the stand-alone cleaning step. Consequently, subsequent blood purification treatment is performed under good conditions. The control unit 13 according to each of the above embodiments executes the stand-alone cleaning step immediately after the flushing step is ended. Alternatively, the stand-alone cleaning step may be executed after another step that is executed after the flushing step.

According to each of the first to fourth embodiments, when the flushing step is executed by the control unit 13, the cleaning solution or the disinfecting solution introduced from the introduction route (the A-solution introduction route La, La1 or the B-solution introduction route Lb, Lb1) is caused to flow through the dialysate introduction line L1 and the drain-liquid discharge line L2. Therefore, the cleaning solution or the disinfecting solution introduced from the introduction route (the A-solution introduction route La, La1 or the B-solution introduction route Lb, Lb1) is discharged to the outside of the apparatus through the flow routes intended for blood purification treatment.

The line section according to each of the first to fourth embodiments includes the bypass line L4 connected to the dialysate introduction line L1 and to the drain-liquid discharge line L2. Furthermore, when the flushing step is executed by the control unit 13, the cleaning solution or the disinfecting solution introduced from the introduction route (the A-solution introduction route La, La1 or the B-solution introduction route Lb, Lb1) is caused to flow through the dialysate introduction line L1, the drain-liquid discharge line L2, and the bypass line L4. Therefore, the cleaning solution or the disinfecting solution introduced from the introduction route (the A-solution introduction route La, La1 or the B-solution introduction route Lb, Lb1) is discharged to the outside of the apparatus through the shortest route.

The delivery unit according to each of the first to fourth embodiments is the duplex pump 7 provided over the dialysate introduction line L1 and the drain-liquid discharge line L2. Therefore, the cleaning solution or the disinfecting solution introduced from the introduction route (the A-solution introduction route La, La1 or the B-solution introduction route Lb, Lb1) is discharged to the outside of the apparatus by using the duplex pump 7, which is intended for blood purification treatment. In replacement of the duplex pump 7, another pump may be employed to discharge the cleaning solution or the disinfecting solution introduced from the introduction route (the A-solution introduction route La, La1 or the B-solution introduction route Lb, Lb1) to the outside of the apparatus in the flushing step.

The introduction route (the A-solution introduction route La and the B-solution introduction route Lb) according to each of the first to fourth embodiments is provided with the infusion pump (the A-solution infusion pump 11 and the B-solution infusion pump 12) that delivers the undiluted dialysate introduced from the introduction port (the A-solution introduction port P1 and the B-solution introduction port P2) to the line section including the dialysate introduction line L1. Therefore, in the flushing step, the cleaning solution or the disinfecting solution flowing in the supply route (R, Ra) is caused to flow into the introduction route (the A-solution introduction route La and the B-solution introduction route Lb) by using the infusion pump (the A-solution infusion pump 11 and the B-solution infusion pump 12).

Furthermore, since the infusion pump (the A-solution infusion pump 11 and the B-solution infusion pump 12) that delivers the undiluted dialysate introduced from the introduction port (the A-solution introduction port P1 and the B-solution introduction port P2) to the line section including the dialysate introduction line L1 is provided, when the duplex pump 7 is activated with the electromagnetic valve V3 open to allow the supply of the clean water (RO water) while the cleaning solution or the disinfecting solution flowing in the supply route (R, Ra) is introduced from the introduction port (the A-solution introduction port P1 and the B-solution introduction port P2) by using the infusion pump (the A-solution infusion pump 11 and the B-solution infusion pump 12), simultaneous introduction of the clean water and the cleaning solution or the disinfecting solution is achieved. In such a case, the cleaning solution or the disinfecting solution flowing in the dialysate introduction line L1 and the drain-liquid discharge line L2 is diluted with the clean water (RO water). Therefore, the duration of the stand-alone cleaning step is reduced, improving the work efficiency.

The undiluted dialysate according to each of the first to fourth embodiments includes the A-solution and the B-solution having different compositions to be generated into respective working dialysates. Furthermore, the introduction port includes at least one of the A-solution introduction port P1 that allows the A-solution flowing in the supply route to be introduced into the apparatus, and the B-solution introduction port P2 that allows the B-solution flowing in the supply route to be introduced into the apparatus. Therefore, the A-solution or the B-solution is introduced into the apparatus assuredly and smoothly.

In particular, according to each of the second and fourth embodiments, the introduction port includes the A-solution introduction port P1 and the B-solution introduction port P2. Furthermore, the control unit 13 prohibits the introduction of the cleaning solution or the disinfecting solution from the B-solution introduction port P2 while the cleaning solution or the disinfecting solution is being introduced from the A-solution introduction port P1, and prohibits the introduction of the cleaning solution or the disinfecting solution from the A-solution introduction port P1 while the cleaning solution or the disinfecting solution is being introduced from the B-solution introduction port P2. Such a configuration prevents the mixing between different cleaning solutions or disinfecting solutions in the line section that may be caused by simultaneous introduction of the different cleaning solutions or disinfecting solutions from the A-solution introduction port P1 and the B-solution introduction port P2 into the line section.

In addition, the control unit 13 according to each of the first to fourth embodiments executes the flushing step if the blood purification apparatus 1 is in the standby step as the standby state in which the line section is filled with the clean water. Such a configuration prevents the mixing between any liquid other than the clean water, specifically the cleaning solution or the disinfecting solution, remaining in the line section and the cleaning solution or the disinfecting solution introduced from the introduction port (the A-solution introduction port P1 or the B-solution introduction port P2) into the line section.

The control unit 13 according to each of the first and second embodiments executes the flushing step if the operator performs the predetermined operation. Such a configuration prevents the execution of the flushing step with a wrong timing. On the other hand, the control unit 13 according to the third embodiment executes the flushing step automatically with reference to the start time or end time on the preset date. Therefore, the flushing step is executed assuredly.

According to the fourth embodiment, the supply route (R1, R2) is connected to the undiluted-solution tank (T1, T2) containing the undiluted dialysate. Furthermore, the control unit 13 executes the flushing step with reference to the step signal received from the supply-side control unit that controls the undiluted-solution tank (T1, T2). Therefore, the flushing step is executed with an appropriate timing. Furthermore, the flushing step is executed assuredly and smoothly.

While some embodiments have been described above, the present invention is not limited thereto. Other possible embodiments are as follows, for example: an embodiment in which the stand-alone cleaning step is not executed after the flushing step, an embodiment in which, in the flushing step, the cleaning solution or the disinfecting solution in the supply route is caused to flow through the bypass line L5 as well as the dialysate introduction line L1 and the drain-liquid discharge line L2 before being discharged to the outside of the apparatus, or an embodiment in which the cleaning solution or the disinfecting solution in the supply route is caused to flow through other lines before being discharged to the outside of the apparatus.

The above embodiments are each applied to an apparatus in which the undiluted dialysate is introduced into relevant lines of the blood purification apparatus 1 through the introduction port (the A-solution introduction port P1 or the B-solution introduction port P2). Alternatively, the present invention may be applied to an apparatus including an introduction port connected to a supply route through which working dialysate is supplied, the introduction port allowing the working dialysate in the supply route to be introduced into the apparatus; an introduction route connected to the introduction port and through which the working dialysate introduced from the introduction port flows into a line section; a valve unit provided to the introduction route and being capable of opening or closing the introduction route by being opened or closed; and a control unit that controls the operation of opening and closing the valve unit, the control unit being capable of executing a flushing step in which when a cleaning solution or a disinfecting solution is caused to flow through the supply route, the valve unit is opened to allow the cleaning solution or the disinfecting solution flowing in the supply route to flow into the introduction route and through the line section to be discharged to the outside of the apparatus.

Furthermore, the A-solution infusion pump 11 and the B-solution infusion pump 12 may be replaced with pumps of another type that deliver the respective undiluted dialysate introduced from the respective introduction ports to the line section including the dialysate introduction line L1. Moreover, the infusion pumps such as the A-solution infusion pump 11 and the B-solution infusion pump 12 may be omitted. In such a case, any of the following embodiments may be employed, for example: an embodiment in which the A-solution or the B-solution is infused into relevant lines of the apparatus by using the duplex pump 7 (the delivery unit), an embodiment in which the A-solution or the B-solution is infused into relevant lines of the apparatus by using a pump provided to the supply route Ra, an embodiment in which the A-solution or the B-solution is infused by making the fluid pressure in the supply route (R, Ra) higher than the fluid pressure in relevant lines of the apparatus.

In a personal dialysis apparatus, as in the above embodiments, a working dialysate needs to be generated by causing the A-solution or the B-solution to flow into the apparatus. Therefore, the A-solution infusion pump 11 and the B-solution infusion pump 12 are essential. However, the present invention is applicable not only to a personal dialysis apparatus but also to blood purification apparatuses of other types, such as a multi-patient dialysis apparatus. Therefore, the present invention does not necessarily require the A-solution infusion pump 11 and the B-solution infusion pump 12. The above embodiments are each applied to a hemodialysis apparatus capable of giving a treatment such as hemodialysis (HD), ECUM, or HDF (hemodiafiltration). Alternatively, the present invention may be applied to a blood purification apparatus capable of giving another blood purification treatment (such as hemofiltration (HF) or continuous slow hemofiltration (CHF)).

The present teaching is also applicable to a blood purification apparatus having a different appearance, additional functions, or the like, as long as the apparatus is capable of executing a flushing step in which when a cleaning solution or a disinfecting solution is caused to flow through the supply route, the valve unit is opened to allow the cleaning solution or the disinfecting solution flowing in the supply route to flow into the introduction route and through the line section to be discharged to an outside of the apparatus.

REFERENCE SIGN LIST 1 blood purification apparatus
2 blood circuit
3 dialyzer (blood purifier)
4 blood pump
5 arterial air-trap chamber
6 venous air-trap chamber
7 duplex pump
8 ultrafiltration pump
9, 10 mixing chamber
11 A-solution infusion pump
12 B-solution infusion pump
13 control unit
R supply route (header)
Ra supply route (branch line)
M display
T undiluted-solution tank
F1, F2 filter
P1 A-solution introduction port
P2 B-solution introduction port
La, La1, La2 A-solution introduction route
Lb, Lb1, Lb2 B-solution introduction route
V7, V8 electromagnetic valve (valve unit)
h1, h2 nozzle

What is claimed is:

1. A blood purification apparatus comprising:
a line section through which working dialysate to be introduced into a blood purifier or drain liquid discharged from the blood purifier is caused to flow, wherein the line section comprises a drain-liquid discharge line;
a delivery unit that delivers liquid in the line section;
an introduction port connected to a supply route through which undiluted dialysate or the working dialysate is supplied, the introduction port allowing the undiluted dialysate or the working dialysate in the supply route to be introduced into the blood purification apparatus;
an introduction route connected to the introduction port and through which the undiluted dialysate or the working dialysate introduced from the introduction port flows into the line section;
a valve unit provided to the introduction route and being capable of opening or closing the introduction route by being opened or closed; and
a control unit configured to:
control an operation of opening or closing the valve unit, and
execute a flushing step in which when a cleaning solution or a disinfecting solution is caused to flow through the supply route, the valve unit is opened to allow the cleaning solution or the disinfecting solution flowing in the supply route to flow into the introduction route and through the line section to be discharged to an outside of the blood purification apparatus, wherein the flushing step is executed during a cleaning step or a disinfecting step of the supply route;
wherein the drain-liquid discharge line discharges the drain liquid from the blood purifier to the outside of the blood purification apparatus and the cleaning solution or the disinfecting solution is discharged to the outside of the blood purification apparatus through the drain-liquid discharge line during the flushing step.

2. The blood purification apparatus according to claim 1, wherein after the flushing step is ended, the control unit executes a stand-alone cleaning step in which the line section is cleaned with the valve unit closed.

3. The blood purification apparatus according to claim 1, wherein the introduction route allows the undiluted dialysate flowing in the supply route to be introduced into the blood purification apparatus; wherein the line section includes a dialysate introduction line into which clean water is introduced and in which the undiluted dialysate introduced from the introduction route is diluted with the clean water into the working dialysate, the working dialysate being introduced into the blood purifier through the dialysate introduction line, the line section further including a drain-liquid discharge line through which the drain liquid from the blood purifier is discharged; and wherein when the flushing step is executed by the control unit, the cleaning solution or the disinfecting solution introduced from the introduction route is caused to flow through the dialysate introduction line and the drain-liquid discharge line.

4. The blood purification apparatus according to claim 3, wherein the line section includes a bypass line connected to the dialysate introduction line and to the drain-liquid discharge line; and wherein when the flushing step is executed by the control unit, the cleaning solution or the disinfecting solution introduced from the introduction route is caused to flow through the dialysate introduction line, the drain-liquid discharge line, and the bypass line.

5. The blood purification apparatus according to claim 3, wherein the delivery unit is a duplex pump provided over the dialysate introduction line and the drain-liquid discharge line.

6. The blood purification apparatus according to claim 1, wherein the introduction route is provided with an infusion pump that delivers the undiluted dialysate or the working dialysate introduced from the introduction port to the line section.

7. The blood purification apparatus according to claim 3, wherein the undiluted dialysate includes an A-solution and a B-solution having different compositions to be generated into respective working dialysates; and wherein the introduction port includes at least one of an A-solution introduction port that allows the A-solution flowing in the supply route to be introduced into the apparatus, and a B-solution introduction port that allows the B-solution flowing in the supply route to be introduced into the blood purification apparatus.

8. The blood purification apparatus according to claim 7, wherein the introduction port includes the A-solution introduction port and the B-solution introduction port; and wherein the control unit prohibits the introduction of the cleaning solution or the disinfecting solution from the B-solution introduction port while the cleaning solution or the disinfecting solution is being introduced from the A-solution introduction port, and prohibits the introduction of the cleaning solution or the disinfecting solution from the A-solution introduction port while the cleaning solution or the disinfecting solution is being introduced from the B-solution introduction port.

9. The blood purification apparatus according to claim 1, wherein the control unit executes the flushing step if the blood purification apparatus is in a standby step as a standby state in which the line section is filled with clean water.

10. The blood purification apparatus according to claim 1, wherein the control unit executes the flushing step if an operator performs a predetermined operation.

11. The blood purification apparatus according to claim 1, wherein the control unit executes the flushing step automatically with reference to a start time or end time on a preset date.

12. The blood purification apparatus according to claim 1, wherein the supply route is connected to an undiluted-solution tank containing the undiluted dialysate; and wherein the control unit executes the flushing step with reference to a step signal received from a supply-side control unit that controls the undiluted-solution tank.

* * * * *